(12) United States Patent
Lay et al.

(10) Patent No.: US 11,200,667 B2
(45) Date of Patent: Dec. 14, 2021

(54) DETECTION OF PROSTATE CANCER IN MULTI-PARAMETRIC MRI USING RANDOM FOREST WITH INSTANCE WEIGHTING AND MR PROSTATE SEGMENTATION BY DEEP LEARNING WITH HOLISTICALLY-NESTED NETWORKS

(71) Applicant: The United States of America, as represented by the Secretary, Department of Health and Human Services, Bethesda, MD (US)

(72) Inventors: Nathan S. Lay, Bethesda, MD (US); Yohannes Tsehay, Silver Spring, MD (US); Ronald M. Summers, Potomac, MD (US); Baris Turkbey, Rockville, MD (US); Matthew Greer, Bethesda, MD (US); Ruida Cheng, Bethesda, MD (US); Holger Roth, Bavaria (DE); Matthew J. McAuliffe, Bethesda, MD (US); Sonia Gaur, Bethesda, MD (US); Francesca Mertan, Bethesda, MD (US); Peter Choyke, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 78 days.

(21) Appl. No.: 16/488,127

(22) PCT Filed: Feb. 22, 2018

(86) PCT No.: PCT/US2018/019249
§ 371 (c)(1),
(2) Date: Aug. 22, 2019

(87) PCT Pub. No.: WO2018/156778
PCT Pub. Date: Aug. 30, 2018

(65) Prior Publication Data
US 2019/0370965 A1  Dec. 5, 2019

Related U.S. Application Data

(60) Provisional application No. 62/462,256, filed on Feb. 22, 2017.

(51) Int. Cl.
*G06T 7/00* (2017.01)
*G06N 20/00* (2019.01)

(52) U.S. Cl.
CPC ............ *G06T 7/0012* (2013.01); *G06N 20/00* (2019.01); *G06T 2207/10088* (2013.01);
(Continued)

(58) Field of Classification Search
CPC ......... G06T 7/0012; G06T 2207/10088; G06T 2207/20081; G06T 2207/20084;
(Continued)

(56) References Cited

U.S. PATENT DOCUMENTS

| 8,204,315 B2 * | 6/2012 | Madabhushi | G06K 9/6224 382/224 |
| 2012/0155734 A1 * | 6/2012 | Barratt | G06T 7/344 382/131 |

(Continued)

FOREIGN PATENT DOCUMENTS

| WO | WO-2012097336 A1 * | 7/2012 | ........... G06K 9/6256 |
| WO | WO-2013028762 A1 * | 2/2013 | ............. A61B 6/467 |
| WO | WO-2017132345 A1 * | 8/2017 | ........... A61B 5/6852 |

OTHER PUBLICATIONS

Auto-Context and Its Application to High-Level Vision Tasks and 3D Brain Image Segmentation (Year: 2010).*
(Continued)

*Primary Examiner* — Nizar N Sivji
(74) *Attorney, Agent, or Firm* — Leydig, Voit & Mayer, Ltd.

(57) ABSTRACT

Disclosed prostate computer aided diagnosis (CAD) systems employ a Random Forest classifier to detect prostate cancer.
(Continued)

System classify individual pixels inside the prostate as potential sites of cancer using a combination of spatial, intensity and texture features extracted from three sequences. The Random Forest training considers instance-level weighting for equal treatment of small and large cancerous lesions and small and large prostate backgrounds. Two other approaches are based on an AutoContext pipeline intended to make better use of sequence-specific patterns. Also disclosed are methods and systems for accurate automatic segmentation of the prostate in MRI. Methods can include both patch-based and holistic (image-to-image) deep learning methods for segmentation of the prostate. A patch-based convolutional network aims to refine the prostate contour given an initialization. A method for end- to-end prostate segmentation integrates holistically nested edge detection with fully convolutional networks. HNNs automatically learn a hierarchical representation that improve prostate boundary detection.

9 Claims, 21 Drawing Sheets

(52) U.S. Cl.
CPC ............... *G06T 2207/20081* (2013.01); *G06T 2207/20084* (2013.01); *G06T 2207/30081* (2013.01); *G06T 2207/30096* (2013.01)

(58) Field of Classification Search
CPC ........... G06T 2207/30081; G06T 2207/30096; G06N 20/00
See application file for complete search history.

(56) References Cited

U.S. PATENT DOCUMENTS

| | | | |
|---|---|---|---|
| 2014/0037172 A1* | 2/2014 | Madabhushi | G06K 9/6251 382/131 |
| 2014/0270495 A1* | 9/2014 | Tu | G06T 7/11 382/160 |

OTHER PUBLICATIONS

Quantitative Analysis of Multiparametric Prostate MR Images: Differentiation between Prostate Cancer and Normal Tissue and Correlation with Gleason Score—A Computer-aided Diagnosis Development Study1 (Year: 2013).*
Consensus of Ambiguity: Theory and Application of Active Learning for Biomedical Image Analysis (Year: 2010).*
Computerized Detection, Segmentation and Classification of Digital Pathology: Case Study in Prostate Cancer (Year: 2011).*
MRI-based prostate cancer detection with high-level representation and hierarchical classification (Year: 2017).*
Molecular imaging and fusion targeted biopsy of the prostate (Year: 2017).*
Automated 2D segmentation of Prostate in T2-weighted MRI scans (Year: 2017).*
Prostate Cancer Detection via a Quantitative Radiomics-Driven Conditional Random Field Framework (Year: 2015).*
Multiple Clustered Instance Learning for Histopathology Cancer Image Classification, Segmentation and Clustering (Year: 2012).*
International Search Report and Written Opinion for related International Application No. PCT/US2018/019249, dated Jun. 29, 2018, 18 pages.
Kwak et al., "Automated prostate cancer detection using T2-weighted and high-b-value diffusion-weighted magnetic resonance imaging," *Med. Phys.* 42(5):2368-2378 (May 2015).
Litjens et al., "Computer-Aided Detection of Prostate Cancer in MRI," *IEEE Transactons on Medical Imaging*, 33(5):1083-1092 (May 2014).
Rampun et al., "Computer-Aided Detection of Prostate Cancer in T2-Weighted MRI within the Peripheral Zone," *Physics in Medicine and Biology*, 61(3):4796-4825 (Jul. 2016).
Qian et al., "In vivo MRI based prostate cancer localization with random forests and auto-context model," *Comput Med Imaging Graph.*, 52:44-57 (Sep. 2016).

* cited by examiner

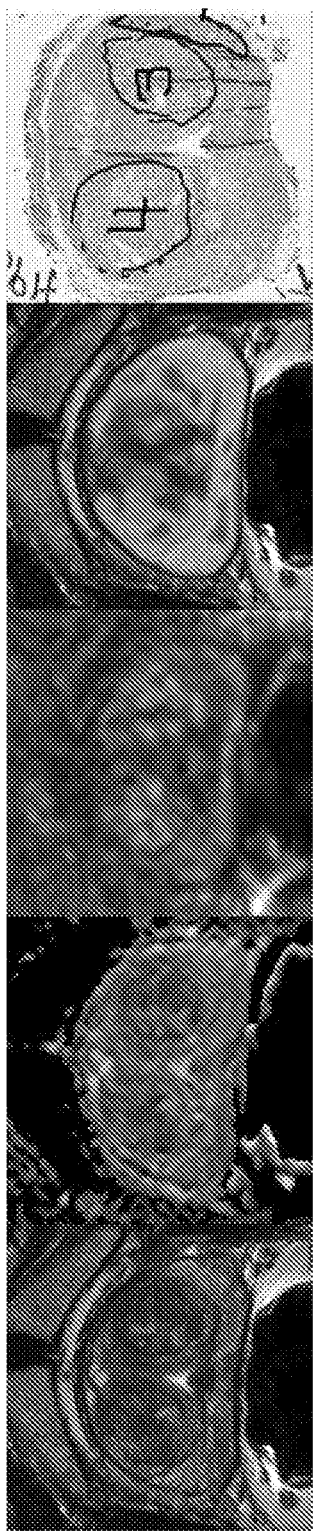
FIG. 9

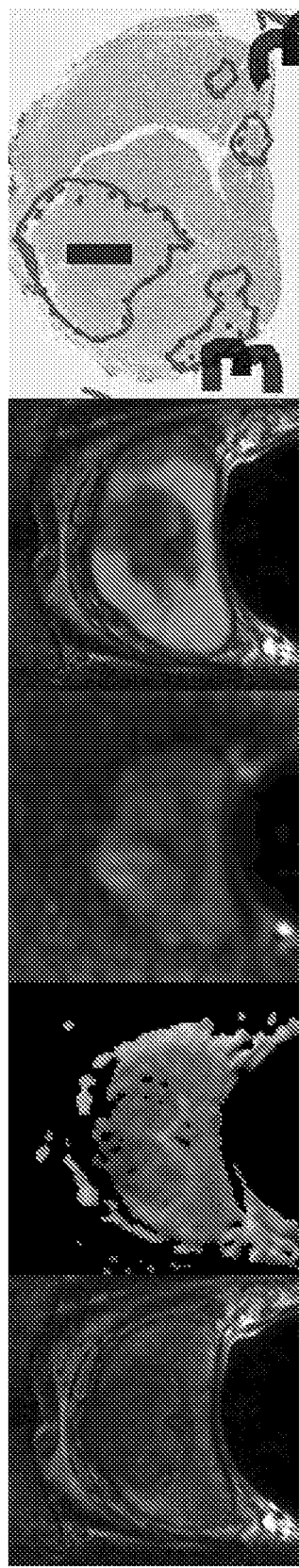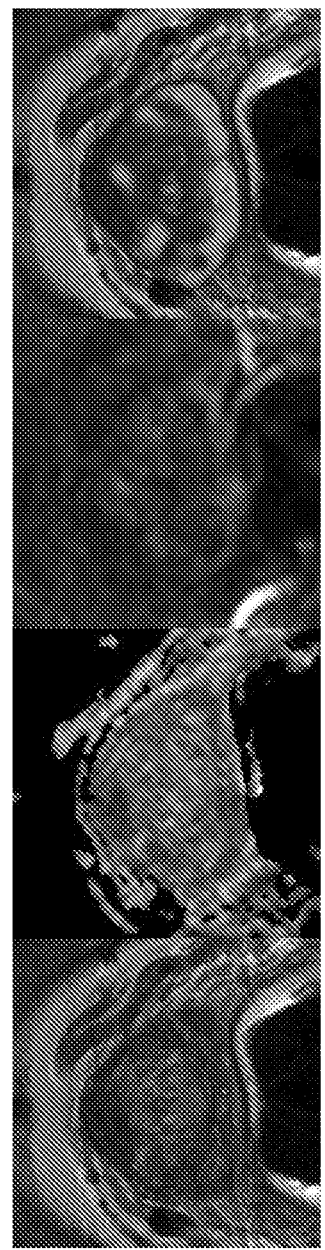
FIG. 10

DETECTION OF PROSTATE CANCER IN MULTI-PARAMETRIC MRI USING RANDOM FOREST WITH INSTANCE WEIGHTING AND MR PROSTATE SEGMENTATION BY DEEP LEARNING WITH HOLISTICALLY-NESTED NETWORKS

STATEMENT OF GOVERNMENT SUPPORT

This invention was made with Government support under project number 1Z01 CL040004 by the National Institutes of Health, Clinical Center and National Cancer Institute. The Government has certain rights in the invention.

CROSS-REFERENCE TO RELATED APPLICATIONS

This is the U.S. National Stage of International Application No. PCT/US2018/019249, filed Feb. 22, 2018, which was published in English under PCT Article 21(2), which in turn claims the benefit of U.S. Provisional Patent Application No. 62/462,256 filed Feb. 22, 2017, which is incorporated by referenced herein in its entirety.

FIELD

This disclosure relates to prostate cancer computer-aided diagnosis (CAD) systems, such as systems that can recommend biopsy sites in multi-parametric MRI (mpMRI) scans, as well as to MR prostate segmentation technologies.

BACKGROUND

Prostate cancer is the sixth most common cancer worldwide. A widely used method to diagnose prostate cancer involves randomly biopsying the prostate in 10-12 locations throughout the prostate. Due to their random nature, biopsies can miss clinically significant lesions and result either in false negatives or inappropriate downgrading the cancer. Incidental findings of prostate cancer are also frequent and may result in overdiagnosis and overtreatment. More recently, multi-parametric MRI (mpMRI) has been demonstrated to be the most accurate imaging technique to detect prostate cancer. mpMRI guided biopsies improve sensitivity for clinically significant prostate cancer while limiting overdiagnosis.

Segmentation of T2 weighted (T2w) prostate MR images is important for accurate therapy planning and aiding automated prostate cancer diagnosis algorithms. It plays a crucial role in many existing and developing clinical applications. For example, radiotherapy planning for prostate cancer treatment can require accurate delineation of the prostate in imaging data (mostly MR and CT). In current practice, this is typically achieved by manual contouring of prostate in a slice-by-slice manner using either the axial, sagittal, coronal view or a combination of different views. This manual contouring is labor intensive and is prone to inter- and intra-observer variance. Accurate and automatic prostate segmentation based on 3D MR images would seemingly offer many benefits such as efficiency, reproducibility and elimination of inconsistencies or biases between operators performing manual segmentation. However, automated segmentation is challenging due to the heterogeneous intensity distribution of the prostate MR image and the complex anatomical structures within and surrounding the prostate.

SUMMARY

Disclosed herein are exemplary prostate computer aided diagnosis (CAD) systems and methods, some of which employ a Random Forest classifier to detect prostate cancer. An example system classifies individual pixels inside the prostate as potential sites of cancer using a combination of spatial, intensity and texture features extracted from three imaging sequences: T2W, ADC, and b-2000 images. The Random Forest training considers instance-level weighting for equal treatment of small and large cancerous lesions as well as small and large prostate backgrounds. Two other approaches can also be included, and are based on an AutoContext pipeline intended to make better use of sequence-specific patterns. One pipeline uses Random Forest on individual sequences while the other uses an image filter described in this work to produce probability map-like images. Five permutations of two-fold cross validation were used to assess performance for overall cancer detection and Gleason grade-specific detection. A receiver operating characteristic (ROC) curve and Gleason grade-specific free response ROC (FROC) curves were plotted for the Random Forest and other two methods. These were compared to a previously-published CAD approach based on support vector machine (SVM) evaluated on the same data.

The pipeline using Random Forest achieved an AUC of 0.93 with detection rate of 91% at 20% false positive rate with corresponding detection rate of 91% at an average number of false positives per patient of 14 in the Gleason$\geq$7 FROC analysis. This compares favorably with the SVM-based approach which has an AUC of 0.86 with detection rate 81% at 20% false positive rate and a corresponding detection rate of 92% at an average false positives per patient of 19 for the Gleason$\geq$7 FROC analysis. Significance was established for the Gleason$\geq$7 FROC curves using JAFROC2 for the Random Forest vs. the SVM method. The Random Forest performance was statistically significantly different than SVM in nine out of the ten experiments. The AutoContext-based methods were not statistically different than Random Forest although the image-filtering version was more stable in performance and performed better for the three Gleason 10 lesions in the data set.

The Random Forest, features, sampling strategy, and instance-level weighting can help improve prostate cancer detection performance in comparison to SVM. A first stage detector using a simple image filtering technique to highlight likely regions of prostate cancer can help somewhat with learning stability over using a learning-based approach owing to visibility and ambiguity of annotations in each sequence. These limitations are not present with the image filtering approach.

Also disclosed herein are methods and systems for accurate automatic segmentation of the prostate in magnetic resonance images (MRI), which is a challenging task due to the high variability of prostate anatomic structure. Artifacts such as noise and similar signal intensity of tissues around the prostate boundary inhibit traditional segmentation methods from achieving high accuracy. In the disclosed technology, we describe both patch-based and holistic (image-to-image) deep learning methods for segmentation of the prostate. We first disclose a patch-based convolutional network that aims to refine the prostate contour given an initialization. Secondly, we disclose a method for end-to-end prostate segmentation by integrating holistically nested edge detection with fully convolutional networks. Holistically nested networks (HNN) automatically learn a hierarchical representation that can improve prostate boundary detection. Quantitative evaluation is performed on the MRI scans of 250 patients in 5-fold cross-validation.

The foregoing and other objects, features, and advantages of the disclosed technology will become more apparent from the following detailed description, which proceeds with reference to the accompanying figures.

BRIEF DESCRIPTION OF THE DRAWINGS

FIG. 9 shows three cases (rows) with prominent false positives. The top row shows the prostate of a 67 year old with numerous false positives in the peripheral zone that render the CAD more difficult to interpret (Index lesion is marked I with Gleason score 7). The second row shows the prostate of another 67 year old with false positives along the midline base and underestimates the tumor burden of lesion 3 and 4 (Index lesion is marked 3 with Gleason score 7). The third row shows the prostate of a 65 year old with several false positives in the right side and transition zone of the prostate (Index lesion is marked I with Gleason score 7).

FIG. 10 shows three cases with false negatives or underestimated tumor burden. The top row shows the prostate of a 50 year old with an underestimated lesion 1 in the transition zone (Index lesion is marked 1 with Gleason score 7). The second row shows the prostate of a 64 year old with lesions 2 and 4 completely missed (Index lesion is marked 2 with Gleason score 7). The third row shows the prostate of a 65 year old with a completely missed transition zone lesion (Index lesion is marked 1 with Gleason score 7). The B2000 image in the third row shows no indication of cancer while ADC and T2W images show low intensity regions that indicate a potential site of cancer.

DETAILED DESCRIPTION

Figure 1:
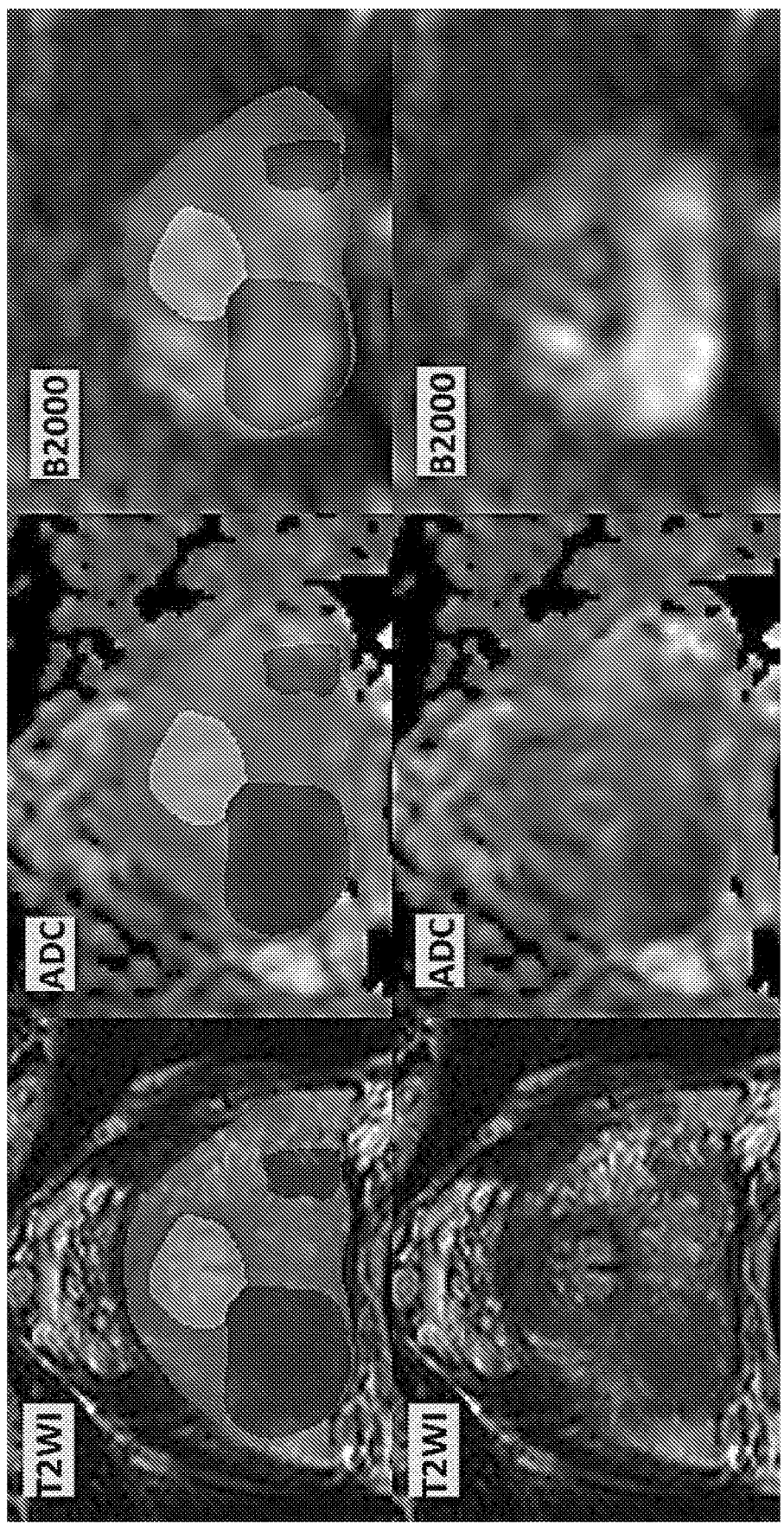
FIG. 1 shows an example of the three sequences (bottom row) and contour annotations (top row). Here the blue is the whole prostate segmentation, green is the transition zone segmentation, and red are cancerous lesions.
Figure 2:
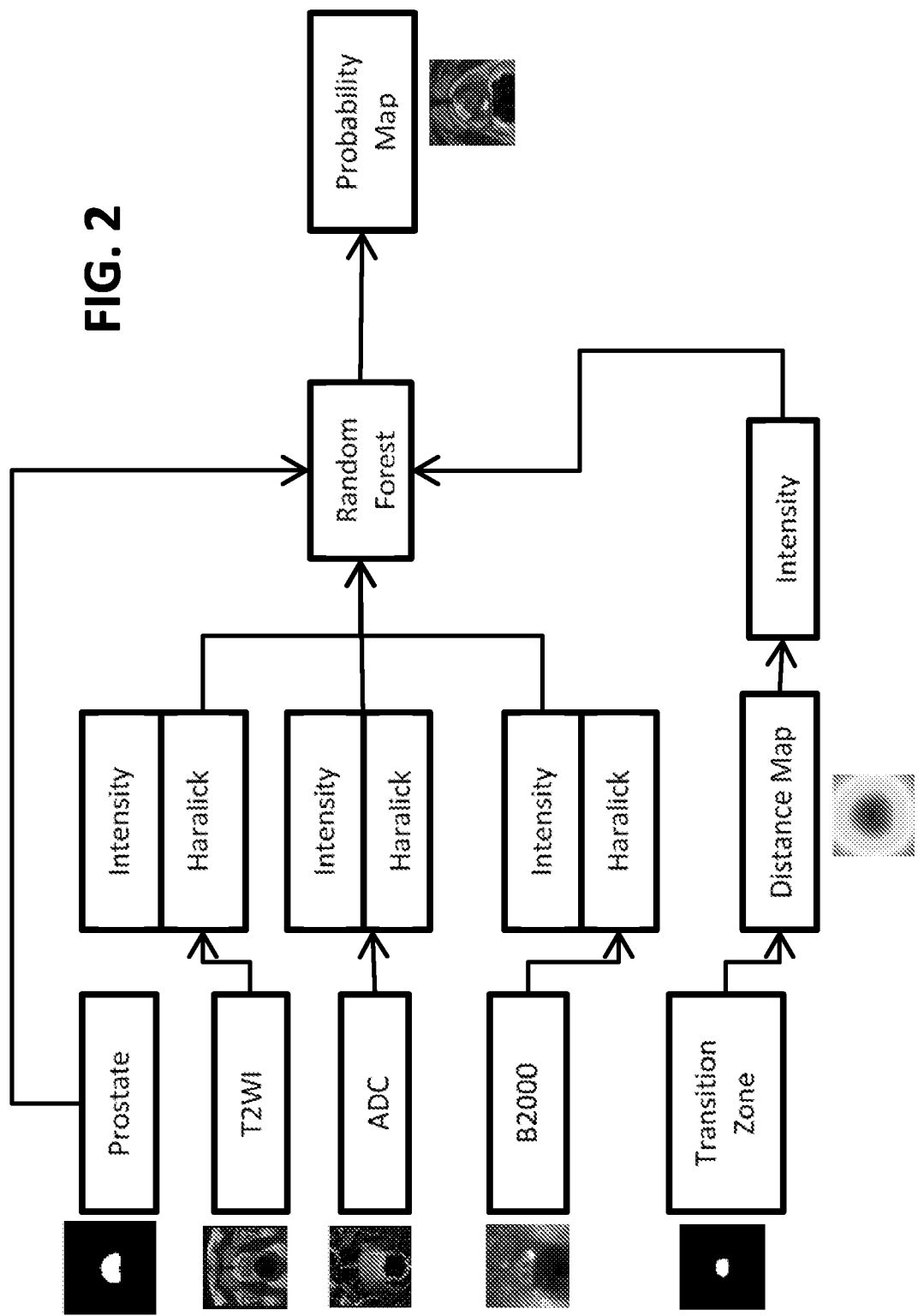
FIG. 2 illustrates a method of prostate computer-aided diagnosis (CAD) using Random Forest.

A widely used method to diagnose prostate cancer involves randomly biopsying the prostate in several locations throughout the prostate. Due to their random nature, biopsies can miss clinically significant lesions and result either in false negatives or inappropriate downgrading the cancer. Incidental findings of prostate cancer are also frequent and may result in overdiagnosis and overtreatment. Multi-parametric magnetic resonance imaging (mpMRI) has been demonstrated to be an accurate imaging technique to detect prostate cancer. mpMRI guided biopsies can improve sensitivity for clinically significant prostate cancer while limiting overdiagnosis. Computer-aided diagnosis (CAD) of prostate cancer can increase sensitivity further. A CAD system can quickly interpret the plethora of images available in mpMRI and assist radiologists with less experience. Sensitivity from mpMRI alone can be as much as 81%.

The technology disclosed herein includes prostate cancer CAD systems for the purpose of recommending biopsy sites. The disclosed CAD systems can utilize learning-based methods, namely Random Forest, and can produce probability images from T2W, ADC and B2000 MRI images. The probability image can then be visualized by a prostate reader. Features of this application include the use of an AutoContext detection pipeline, a sample weighting strategy and the use of various kinds of ground truth information of varying quality. We validate the disclosed CAD on a dataset of 224 patient scans, and compare the performance with a previously-published CAD operating on the same dataset.

Some prostate cancer CAD systems use Support Vector Machine (SVM) with local binary pattern features applied to T2W and B2000 images to predict whether pixels were likely to be cancer or not. An example SVM system was trained against a cohort of 264 patients with recorded biopsy results. Another example prostate CAD system includes a voxel-wise classification approach and a lesion segmentation algorithm. The classifiers used in that example include a linear discriminant classifier, GentleBoost and Random Forest and used T2W, ADC, B800 and dynamic contrast enhanced (DCE) images. The features considered include pixel intensity, relative location in the prostate, texture, blobness and pharmacokinetic heuristics. In another example system, prostate cancer candidates were extracted from ADC using a multi-scale Hessian-based blobness filter and then these candidates were further classified using an LDA classifier with statistics-based features computed from T1W, T2W, DCE, ADC, and Ktrans. While the learning task is slightly different, yet another example approach employs intensity statistics and Haralick texture features to classify Gleason score from MR images using a variety of classifiers. Some such systems use SMOTE to deal with sample imbalance.

The technology disclosed herein can differ from other CAD systems in various ways, such as by using instance-level weighting to deal with label imbalance as well as for fair treatment between small and large cancerous lesions and for fair treatment between small and large prostates. This is one approach to deal with sample imbalance with oversampling techniques. Furthermore, the herein disclosed systems can use several kinds of annotations, such as hand-drawn contours, targeted biopsies, and normal cases, and can also utilize sampling strategies for each these types of annotations. Further, the disclosed technology can use a transition zone distance as a feature to help the model specialize on peripheral and transition zones. This can be more powerful than distance features that only consider distances to the boundary of the prostate.

A study of the herein disclosed technology incorporated 224 patient cases involving 3 types of annotations. These include 53 cases with hand-drawn cancerous lesion contours, 24 normal cases, and 147 MRI-TRUS fusion targeted biopsy cases. All cases additionally include an automatic segmentation of the prostate and transition zone produced by a commercial algorithm with some manual correction by an experienced radiologist. The cancer lesion contours were drawn on T2W images by an experienced radiologist examining mpMRI and biopsy results for these cases. The expertise and time required to manually contour cancerous lesions is generally prohibitive and motivates the use of other available information. Biopsy results are numerous and readily available. They are assumed to be reliable owing to the use of MRI-TRUS fusion to target suspicious regions in the prostate.

Owing to factors such as human error controlling the biopsy needle and image registration problems, MRI-TRUS fusion biopsies can have inaccuracies, however little. There were a total of 200 patients with recorded biopsy results including the 53 patients with hand drawn contours. In each of these patients, biopsy sites were strategically picked from mpMRI by an experienced radiologist prior to the biopsy procedure. Of those biopsy sites 287 were benign and 123 were Gleason 6 or higher. A table of the Gleason grade and zone breakdown is provided in Table 1 below. The remaining 24 normal cases were inspected in mpMRI by an experienced radiologist and were considered to have no visible suspicious lesions. This study additionally considered six test cases selected from consecutive prostate cancer patients who underwent mpMRI and prostatectomy (179 total) for the purpose of comparing with wholemount histopathology in FIGS. 9 and 10.

TABLE 1

| Breakdown of severity of biopsied lesions used in the data set. | | | | | | | |
|---|---|---|---|---|---|---|---|
| Zone | Benign | Gleason 6 | Gleason 7 | Gleason 8 | Gleason 9 | Gleason 10 | Total |
| Peripheral | 183 | 23 | 26 | 12 | 10 | 3 | 257 |
| Transition | 104 | 14 | 18 | 11 | 6 | 0 | 153 |
| Overall | 287 | 37 | 44 | 23 | 16 | 3 | 410 |

The mpMRI images were acquired using a 3T MR scanner (Achieva-TX, Philips Medical Systems, Best, NL) using the anterior half of a 32 channel SENSE cardiac coil (In vivo, Philips Healthcare, Gainesville, Fla.) and an endorectal coil (BPX-30, Medrad, Indianola, Pa.). No pre-examination bowel preparation was required. The balloon of each endorectal coil was distended with approximately 45 ml of perfluorocarbon (Fluorinert FC-770, 3M, St. Paul, Minn.) to reduce imaging artifacts related to air-induced susceptibility. The T2W image was acquired with an echo time, repetition time and section thickness of 4434 msec, 120 msec and 3 mm respectively. The standard DWI was acquired with five evenly spaced b-values (0-750) and high b-value DWI was acquired with b=2000.

According to one embodiment, an exemplary prostate CAD system is based on a pixel-wise Random Forest trained against the three types of annotations. In this example, the CAD makes use of 13 types of Haralick texture features, 4 types of intensity features applied to T2W, ADC, and B2000 images and the signed Euclidean distance to the transition zone. Two other configurations of the CAD based on AutoContext can also be used in some embodiments. These CAD systems additionally use 4 types of intensity features on probability maps from each sequence. Table 2 provides a list of features used in these three systems.

TABLE 2

Features used by the CAD systems. 2D dimensions indicate that the CAD uses the feature and the patch window dimensions used to compute the feature. The Probability Map features are only used in the AutoContext-based methods.

| | Type | T2W | ADC | B2000 | Distance Map | Probability Map |
|---|---|---|---|---|---|---|
| Intensity | Pixel intensity | | | | 1 x 1 pixel | |
| | Mean | 3 mm x 3 mm | | | Not used | 2 mm x 2 mm |
| | Median | | | | | |
| | Variance | | | | | |
| Haralick | Angular Second Moment | | | | | Not used |
| | Contrast | | | | | |
| | Correlation | | | | | |
| | Sum of Squares | | | | | |
| | Inverse Difference Moment | | | | | |
| | Sum Average | | | | | |
| | Sum Variance | | | | | |
| | Sum Entropy | | | | | |
| | Entropy | | | | | |
| | Difference Variance | | | | | |
| | Difference Entropy | | | | | |
| | Information Measure of Correlation 1 | | | | | |
| | Information Measure of Correlation 2 | | | | | |

Haralick texture features are statistics computed on co-occurrence matrices in an attempt to characterize texture. Haralick texture features can be used in characterizing lesions in various structures throughout the body. Haralick features can discriminate between cancerous and non-cancerous prostate lesions in T2W, ADC and dynamic contrast enhanced (DCE) images, and can also discriminate between different Gleason grades of prostate cancer in the same sequences. The ability to characterize texture and discriminate prostate tissue makes them useful in the disclosed technology.

Random Forest comprises an ensemble of random decision trees. The predictions by Random Forest can comprise an average of the predictions of its constituent random trees. A Random Forest can be trained by individually training random trees on random subsets of data. Each random tree can be trained in a similar fashion as a decision tree with the exception that a randomized subset of the features can be used to determine an optimal decision. Optimality of a decision can be determined by the Information Gain.

AutoContext uses a sequence of classifiers to improve classification accuracy in computer vision tasks. Consecutive classifiers use probability maps produced by the previous classifier as a supplemental feature to the image features. The probability maps can highlight relatively prominent structure in an image and make the learning task relatively simpler. The herein disclosed technology can use probability maps independently produced on T2W, ADC and B2000 images, for example, as a feature to a classifier that then produces the final probability map. This can help identify any sequence-specific patterns without correlating any coincidental patterns that might be present on other sequences. However, the final classifier can still overfit coincidental cross-sequence patterns.

Two AutoContext CAD pipelines were examined in conjunction with the herein disclosed technology. The first applies Random Forest on each individual sequence using Haralick, Intensity and signed distance features to produce a sequence-specific probability map, and the second uses simple image filtering to produce pseudo-probability maps for each sequence. These probability maps can then be used as supplemental features to Random Forest along with image features to produce a final probability map. The image filter in the second configuration subtracts the prostate intensity mean from the image and then sets resulting pixels to 0 when they have intensity less than or larger than 0 depending on sequence (T2W, ADC larger than 0, B2000 less than 0). This follows from the observation that lesions visible in T2W and ADC images have relatively lower intensity than normal prostate tissue and that lesions visible in B2000 tend to have relatively higher intensity. This filter rule thus behaves like a simple cancer classifier in each sequence.

Several kinds of training annotations can be used to train the Random Forest, such as hand drawn contours, targeted biopsy results, and normal cases (as three examples). Each tree of the Random Forest can be trained on many uniform randomly sampled patient cases (e.g., 20 in one example), regardless of the annotation type. The positives and negatives used to train the tree can be sampled as follows 1. Contours:

Pixels occurring inside of a hand-drawn cancerous lesion are taken as positive examples. Pixels 3 mm or further away from any hand-drawn cancerous lesion are taken as negative examples.

2. Targeted biopsy results:

Pixels within 5 mm of any biopsy point (regardless of whether they are benign or not) are taken to be positive. Since these biopsies were targeted with the MRI-TRUS fusion approach, the lesions must have appeared abnormal to the radiologist. The task of the CAD is to mimic the radiologist in choosing biopsy sites. The chosen radius follows from the observation that lesions have an average diameter of about 10 mm. It is important to note that no negatives are sampled as the extent of the targeted lesion is not known from the biopsy itself. It may also be possible that other suspicious lesions were not biopsied rendering sampling negatives risky.

3. Normal prostate cases:
Every pixel inside of a normal prostate is taken to be a negative example.

Figure 8:
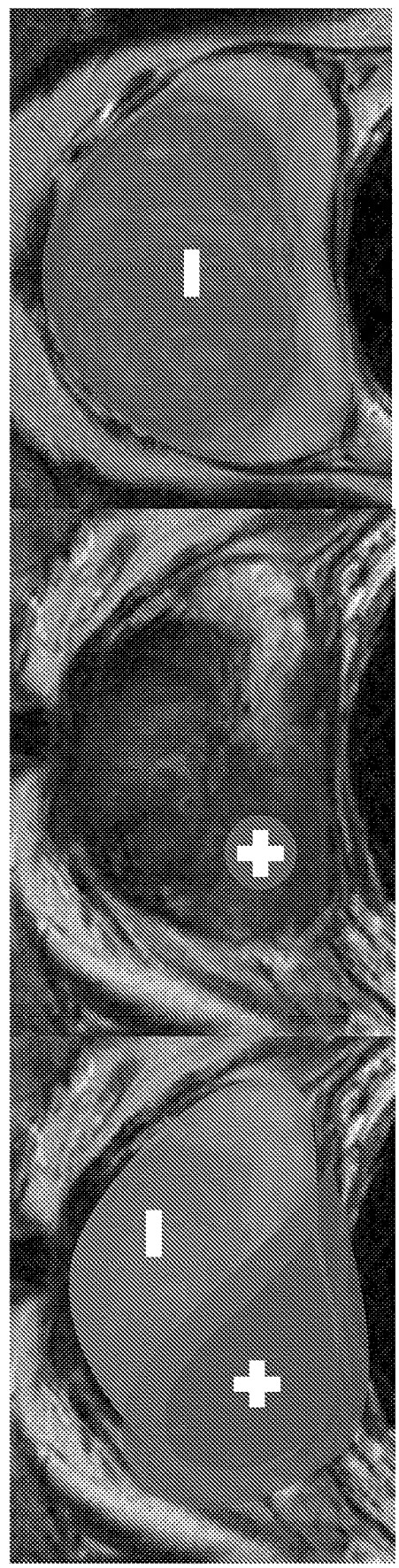
FIG. 8 illustrates a sampling strategy for the three types of annotations. The red regions correspond to positive (cancer) examples, while the green regions correspond to negative (normal) examples. The blue region in the 'Contours' image represents a 3 mm band where neither positive nor negatives examples are sampled. No negative examples are sampled when working with biopsy points.

The three sampling strategies are displayed in FIG. 8. This sampling scheme is unbalanced in a number of ways which could bias a learning-based method. There are an uneven number of positives and negatives and the volumes of prostates and lesions vary by patient and can under-represent or over-represent specific lesions and prostates. The Random Forest in this work can be trained with weighted training examples to counter these potential sources of bias. To work with weighted training examples, the Decision Tree Information Gain function can be modified to be defined as $$IG(X, f, t) = H(p(X)) - \frac{W(X_{f \leq t})}{W(X)} H(p(X_{f \leq t})) - \frac{W(X_{f > t})}{W(X)} H(p(X_{f > t}))$$

where X is a set of training examples (feature vector x, weight w, and class label y) to partition, f is the feature, t is a threshold to partition the training example set, H(p) is a purity function, p is a probability vector and W(X) is a function that sums the weights of the given training examples. These are all given as $$W(X) = \sum_{(x,y,z) \in X} w$$

$$p_k(X) = \frac{W(X_{y=k})}{W(X)}$$

$$H(p) = \sum_{k=1}^{K} p_k (1 - p_k)$$

The purity function used in this Random Forest is the Gini index. This weighted gain is a generalization of the conventional gain function used in Classification and Regression Trees CART where a hard count is replaced by a sum of weights. If the weights are all 1, then this reduces to the CART gain function.

The weights for cancerous lesions in hand-drawn contour cases are taken to be 1/lesion volume while biopsies are taken to be 3/(500*pi), the inverse of which corresponds to the volume of a sphere of radius 5 mm. The negative examples for hand drawn contour cases are taken to be 1/volume of normal prostate tissue and 1/volume of prostate in the case of normal cases. The negative weights are then scaled to have the same sum as the positive weights. This ensures that lesions of any size are treated equally and that positives and negatives are treated equally.

The Random Forest CAD and the two AutoContext methods were trained and evaluated on five permutations of two fold-cross validation on 224 patients (112 training and 112 testing for each permutation). The data were augmented by flipping the images, contours and biopsy points about the y-axis since prostates are symmetric. This effectively doubles the training set size. The cases with contours, targeted biopsy results and normal cases were all independently split into two folds and then concatenated to form the two folds over all patients. This ensures that roughly the same quantities of the three types of annotations are used in each fold. The three systems were additionally compared to a similar CAD system that was evaluated on the same test data but not trained.

Performance was measured in the form of an averaged receiver operating characteristic (ROC) curve and a Gleason grade-specific free-response ROC curve (FROC). Significance was measured between the Random Forest CAD and the SVM CAD FROC curves using JAFROC2.

Owing to the limited number of higher Gleason grade lesions, we consider a two-fold cross validation to maximize the number of lesions of each Gleason grade in both training and testing. We formed five two-fold cross validation sets all resulting from random permutations of the original data set. This helps better demonstrate generalization while leaving a large number of test lesions of various Gleason grades for analysis.

The ROC analysis was performed in 3D. The probability images were taken as a 3D volume and the hand drawn 2D contours were stacked to define 3D cancer volumes. If the $90^{th}$ percentile of the CAD probability scores in a cancer volume exceeds a probability threshold, then this is taken to be a true positive. In other words, if at least 10% of the cancer volume has relatively high probability, then the CAD is said to have detected the cancerous lesion. False positives were computed on normal cases and hand-drawn contour cases by dividing the prostate into 3 mm×3 mm×3 mm cubic cells and evaluating the $90^{th}$ percentile of the CAD probability scores in each cell that do not coincide with a true positive. This coarse treatment of the background eliminates small detections that a prostate reader would effectively ignore. Additionally, a cell is usually at least 3 mm away from a cancer volume to be counted as a false positive. This is meant to account for human error in the annotations.

Like the ROC analysis, the FROC analysis was also performed in 3D. The FROC analysis may be only evaluated on cases with biopsy results which also includes the contour cases. The objective is to quantify performance with respect to Gleason-grade. While Gleason grade is normally expressed in two numbers indicating the two most dominant patterns in the pathology, this work uses the sum of those two numbers ranging from 6-10. Three FROC curves were generated to quantify CAD performance: Actionable, Gleason≥7 and Gleason-specific curves. These can be seen in FIGS. 5, 6 and 7.

All biopsies in this work are targeted and are treated as positive even if they are benign. Every targeted biopsy is said to be actionable since a radiologist deemed these biopsy sites suspicious based on mpMRI. An objective of the disclosed CAD system is to recommend biopsy sites based on mpMRI alone, imitating the best judgement of expert radiologists.

The FROC is generated in three steps. First 3D non-maximum suppression (NMS) is computed on the raw 3D CAD probability map. The NMS uses a window of 10 mm×10 mm×10 mm and produces a small set of points and corresponding probabilities. These roughly reflect local maxima in the probability map. Next a bipartite graph is constructed with one group of vertices being the ground truth biopsy locations and the other group being the NMS detections. An edge is placed between a detection and a ground truth if they are 10 mm or less apart. A weighted maximum matching is computed on the graph to find pairs of detections and ground truths. The weight for each edge is computed based on Gleason-grade and probability using the following function $$w(g, p) = p \times 1.5^{g-6}$$

where g and p are Gleason grade and detection probability respectively. Benign biopsies use the Gleason grade g=0 in this analysis. This is intended to resolve ambiguities where several detections can be assigned to more than one ground truth. This weighting functions prefers higher probability detections be paired with higher Gleason-grade biopsy sites. At this stage, singleton vertices are counted as false positives in the FROC analysis. These vertexes represent detections further than 10 mm away from any ground truth. Lastly, a multi-scale blob-similarity is computed along the axial view of the detection. The blob is measured by convolving a Gaussian kernel on a local patch on the axial view of the probability map centered at the detection. The patch is the same size as the Gaussian kernel and so this operation results in just a single value. Three scales of Gaussian kernel are considered and the maximum convolution is then used as the final probability for the detection. Detections that look locally more like blobs thus have higher probability than those that look less like blobs. These remaining detections and probabilities are then used to determine detection rate.

Figure 3:
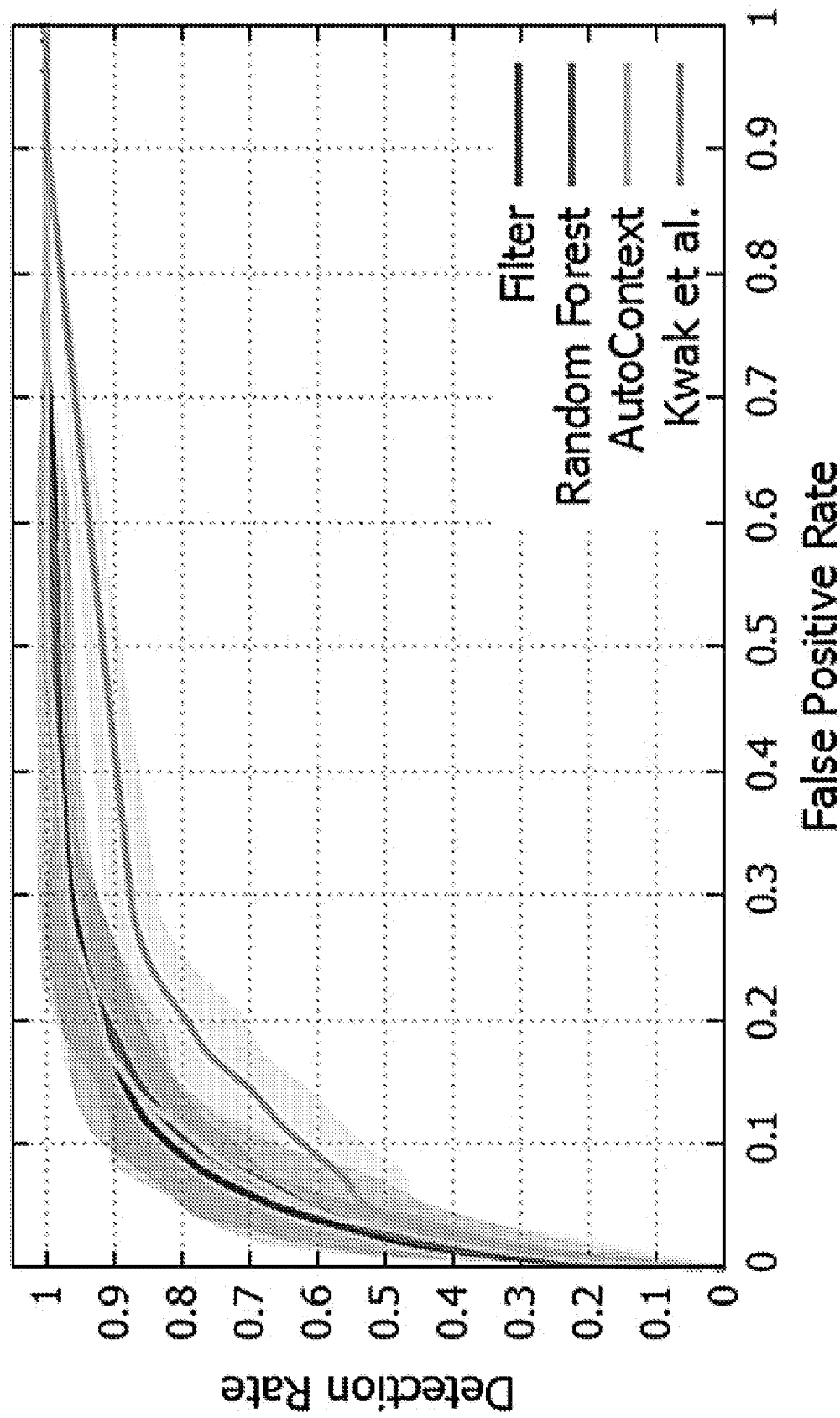
FIG. 3 shows average test ROC Curve of three CAD systems run on five permutations of two fold cross validation. The SVM curve ("Kwak et al.") was run on identical test data but not trained on any of the folds. The corresponding shaded regions are the 95% confidence interval of the detection rate over all the test folds.
Figure 4:
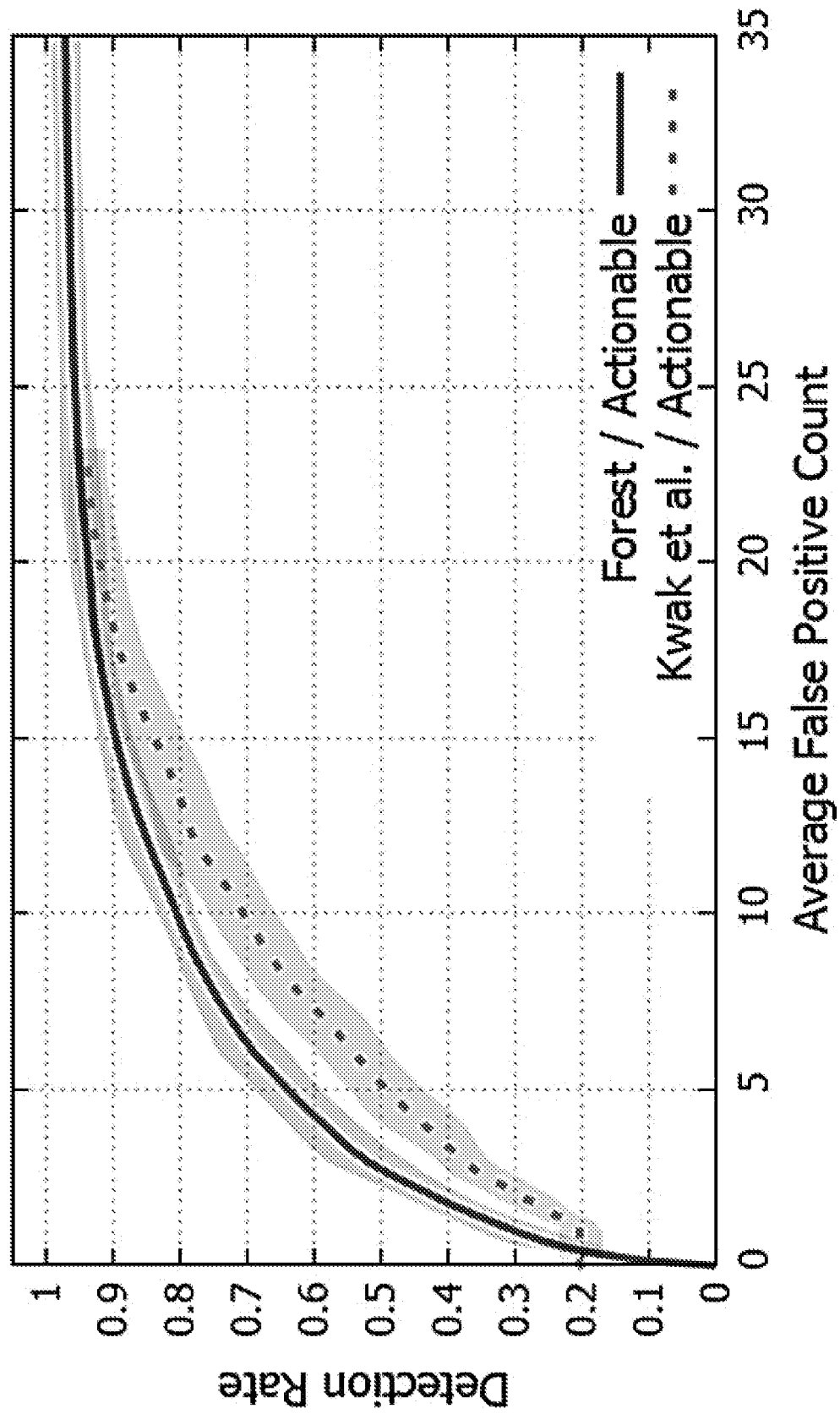
FIG. 4 shows average test FROC Curve of three CAD systems run on five permutations of two fold cross validation. The SVM curve ("Kwak et al.") was run on identical test data but not trained on any of the folds. The corresponding shaded regions are the 95% confidence interval of the detection rate over all the test folds.
Figure 5:
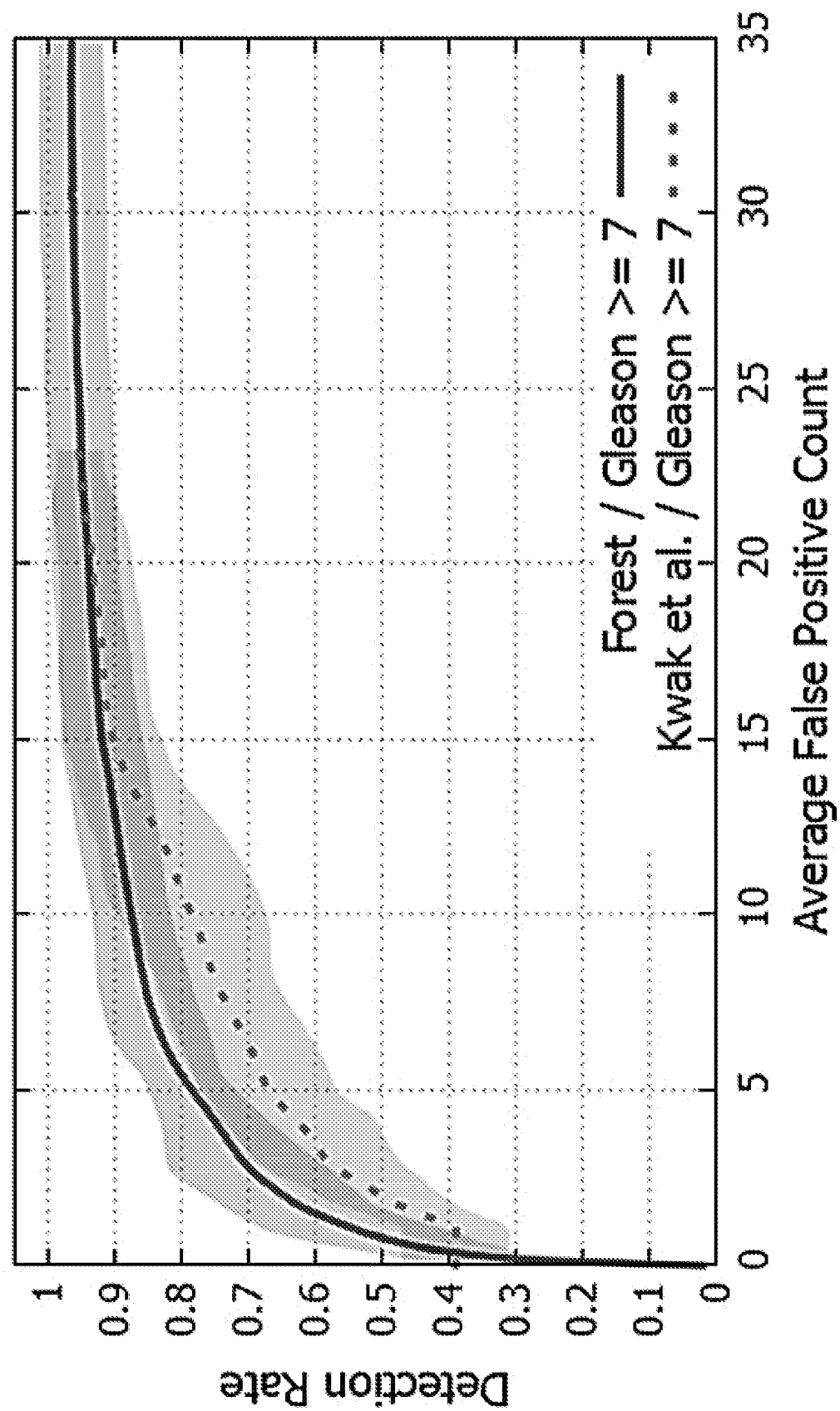
FIG. 5 shows average FROC curve of detections of cancerous lesions Gleason 3+4, 4+3 or higher. The SVM curve ("Kwak et al.") was run on identical test data but not trained on any of the folds. The corresponding shaded regions are the 95% confidence interval of the detection rate over all the test folds.
Figure 6:
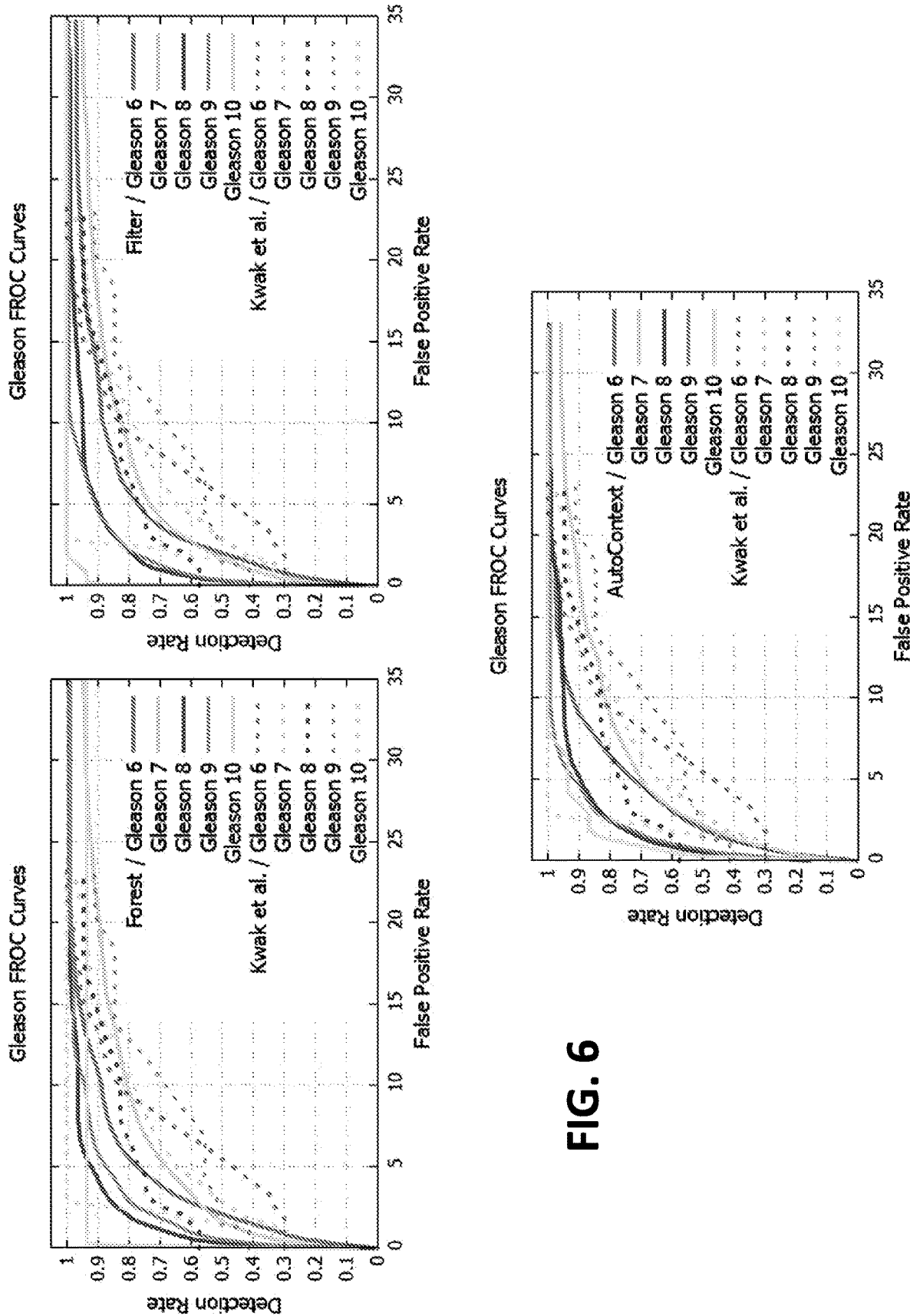
FIG. 6 shows average test FROC curve over five permutations of two fold cross validation and plotted with respect to Gleason grade for Random Forest (Forest), filter-based AutoContext (Filter) and Random Forest-based AutoContext (AutoContext). Random Forest struggles with Gleason 7 lesions and Gleason 10 while Filter and AutoContext approaches struggle with Gleason 7.

The pipeline using the Random Forest detector in the first stage achieved an AUC of 0.93 with a detection rate of 89% and at a false positive rate of 20% for the ROC analysis. This corresponds to 92% detection rate and an average of 13 false positives per patient in the Gleason≥7 FROC analysis. The image filter-based detector achieved a similar AUC of 0.93 with a detection rate of 91% at the same false positive rate on the ROC curve while achieving a corresponding detection rate of 91% and an average number of false positives per patient of 13 at the same threshold in the Gleason≥7 FROC analysis. Both methods are comparable to the methods that do not use probability map features. The Random Forest lacking probability map features achieved an AUC of 0.93 with detection rate 91% at the same false positive rate with corresponding detection rate of 90% and average number of false positives per patient of 14 in the Gleason≥7 FROC analysis. The SVM approach had an AUC of 0.86 with detection rate 81% in the ROC analysis at a false positive rate of 20% and corresponding detection rate of 92% with average false positives per patient of 19 for the Gleason≥7 FROC analysis. All four ROC curves are shown in FIG. 3. FIGS. 4, 5 and 6 show FROC curves for Actionable, Gleason≥7 and fixed Gleason grade detections. Only the filter-based method is considered as it performs the best of all methods in the ROC analysis. Significance was established for the Gleason≥7 FROC curves using JAFROC2 for the filter-based CAD vs. the SVM method. The Random Forest performance was statistically significantly different in 9 out of 10 experiments.

A histogram of the frequency of features used in the CAD selected by Random Forest was computed. The top 5 most selected features by Random Forest were the signed distance to the transition zone, the T2W mean and median, the B2000 median and the ADC median. The distance map feature was twice as likely to be picked as T2W mean and is especially useful to differentiate between the transition zone and peripheral zone. Haralick features are less frequently selected but all 39 are consistently picked by the Random Forest.

Figure 7:
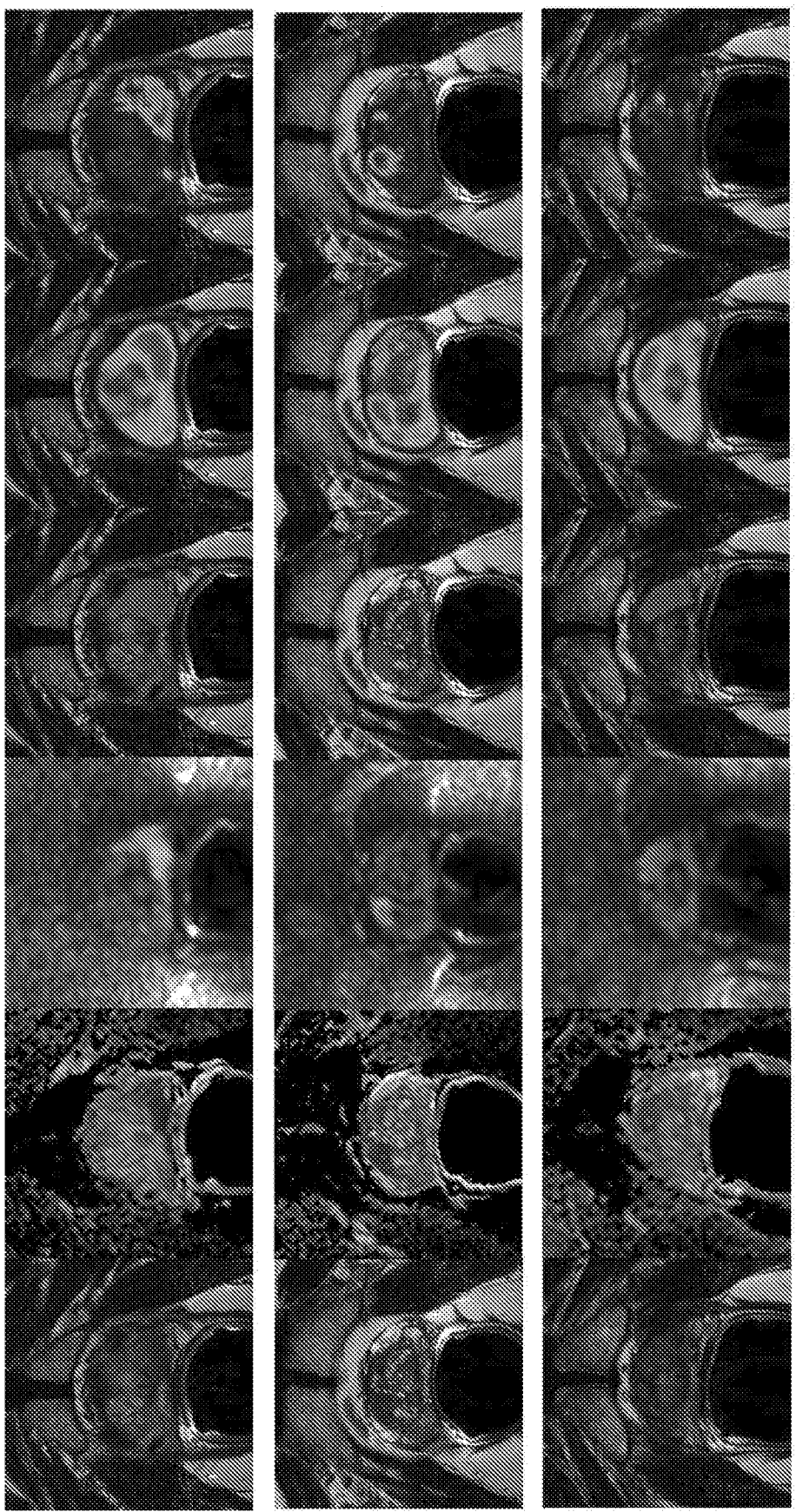
FIG. 7 shows three examples (rows) of input images, annotations, and prostate CAD probability maps based on the herein disclosed CAD systems and from an SVM system ("Jin Tae el al."). The red region in the "Annotation" column is the hand-drawn cancerous lesion annotation. The red regions in the "Probability Map" column denote higher predicted probability of cancer while green and blue denote low predicted probability of cancer. Row 1 is an example of a 74 year old patient with a cancerous lesion in the left apical-mid peripheral zone (Gleason 9). Row 2 shows a 63 year old patient with a cancerous lesion in the right mid-base anterior transition zone (Gleason 7). Lastly, row 3 shows a 49 year old patient with a cancerous lesion in the left apical-mid anterior transition zone (Gleason 7).

FIG. 7 shows the various sequences, annotations and CAD probability maps from Random Forest and the previous CAD. FIGS. 9 and 10 show failure modes of the Random Forest CAD where FIG. 9 shows prominent false positives and FIG. 10 shows missed cancerous lesions. The cases shown in these figures are test cases with whole mount histopathology and were not included in the training or testing sets considered in experiments in this work.

FIG. 8 shows three sampling strategies employed by the CAD during training. These are described above.

The three Random Forest CAD systems performed similarly. The filter-based CAD had a slightly narrower confidence region. It was also more consistent than the other CAD systems since its performance varied less with different training sets. The AutoContext and Random Forest CAD systems varied more although AutoContext was worse than Random Forest with respect to stability. The performance stability of the filter-based method could be attributed to better detection of lesions in the first stage. The filter-based approach attempts to highlight relatively low or high intensity regions in each sequence directly without the use of annotations. Annotations can be problematic in mpMRI as not all lesions are visible in all sequences. Thus, the learning task for specific sequences is more challenging as an annotation may refer to a lesion that is not visible.

All three CADs outperform the SVM-based method. This may be due to a combination of the use of different features, different sequences (the SVM-based method does not use ADC), a different classifier, and different annotations. The SVM-based method uses only biopsies for training data. The data set was selected using inclusion and exclusion criteria to meet specific criteria to reduce ambiguities. This selection could bias the resulting model to specific kinds of prostate cancer configurations. In contrast, this work uses all available training data in three different forms to improve generalizability. Consequently, this work generally outperforms the CAD of the SVM-based method. There are other algorithmic differences that can account for such performance differences. Aside from using a different classifier and different features, one noteworthy difference is the lack of transition zone information in the SVM-based method. This feature is especially useful for learning specialized rules for transition and peripheral zones.

The three CADs in this work outperform the SVM-based method with respect to recommending biopsy sites (whether benign or malignant). The performance for recommending suspicious actionable sites is worse than for recommending biopsy sites for Gleason≥7 lesions. Confusingly, FIG. 6 indicates that all CADs are slightly more performant for Gleason 6, than for Gleason 7. The relatively good performance on Gleason 6 also means that the suspicious lesions found to be benign account for the relatively poorer performance in FIG. 4.

Gleason 7 lesions are problematic for the Random Forest CAD systems. This can be seen in FIG. 7 where all three CAD systems perform comparable to the SVM-based method. This is mainly due to the CAD missing Gleason 7 transition zone lesions. One possible explanation is that some transition zone lesions could be mistaken for fibromuscular stroma. Both structures share similarities such as relatively low intensity. Another possible explanation is the sensitivity of the CAD to the geometric features. Poor transition zone segmentations may cause the CAD to miss transition zone lesions. Transition zone distance features are also in mm units. This could be problematic for unusually large or small prostates. A possible solution to this particular problem is to normalize the distance features. The CAD systems described in this work are still at risk of overfitting cross-sequence patterns. Some false negative cases have been observed to show little or no indication of cancer in high b-value images while having prominent cancerous appearance in one or both of T2W and ADC images. A larger training set with these kinds of images may help CAD systems generalize better. In the case of the AutoContext-based CADs, using a pre-determined decision fusion rule may be more robust as these CADs are still liable to learn coincidental patterns in the training set.

The frequency at which a feature is selected signifies its relative importance. The frequent selection of distance map features demonstrates the added value of anatomical knowledge. Generally lesions found in either one of the zones have similar intensity characteristics, but the backgrounds surrounding the two different regions are visually distinct. The low or high intensity appearance of cancerous lesions in T2W, ADC and B2000 images is consistent with the frequent selection of intensity features from the image sequences. Although individual Haralick features are relatively less frequently selected, there is consistency in the overall selection pattern of all the texture features which indicates that they are all equally relevant for prostate CAD. This is a surprising finding since Haralick texture features have been demonstrated to discriminate between cancerous and non-cancerous prostate tissue as well as between cancerous tissues of differing Gleason grades.

This work introduced three forms of prostate CAD system, the first of which that use the transition zone for features, AutoContext and three types of annotations of various qualities. The CAD system employs a strategy for sample imbalance, using instance-level weighting for fair treatment of all cancerous lesions and normal prostate tissue regardless of volume. The three prostate CAD systems presented here all performed similarly with the filter-based CAD exhibiting slightly more consistent performance. All three CAD systems significantly outperform an SVM-based method on the same data set under the same evaluation methodology.

MR Prostate Segmentation by Deep Learning with Holistically-Nested Networks

Segmentation of T2 weighted (T2w) prostate MR images is important for accurate therapy planning and aiding automated prostate cancer diagnosis algorithms. It plays a crucial role in many existing and developing clinical applications. For example, radiotherapy planning for prostate cancer treatment can require accurate delineation of the prostate in imaging data (mostly MR and CT). In current practice, this is typically achieved by manual contouring of prostate in a slice-by-slice manner using either the axial, sagittal, coronal view or a combination of different views. This manual contouring is labor intensive and is prone to inter- and intra-observer variance. Accurate and automatic prostate segmentation based on 3D MR images would seemingly offer many benefits such as efficiency, reproducibility and elimination of inconsistencies or biases between operators performing manual segmentation. However, automated segmentation is challenging due to the heterogeneous intensity distribution of the prostate MR image and the complex anatomical structures within and surrounding the prostate.

Some methods of automatic prostate segmentation of MR images focuses on atlas, shape and machine learning models. One example comprises an automatic segmentation method based on atlas matching. The atlas consists of a set of prostate MR images and corresponding pre-labeled binary images. Non-rigid registration is used to register the patient image with the atlas images. The best match atlas images are selected and the segmentation is an average of the resulting deformed label images and thresholding value by a majority voting rule. Shape-based models can also be used in MRI prostate segmentation. Another example comprises an automated segmentation model based on normalized gradient field cross-correlation for initialization, and a graph-search based framework for refinement. Another example uses texture features from approximation coefficients of the Haar wavelet transform for propagation of a shape, and Active Appearance Model (AAM) to segment the prostate. Another method extends the traditional AAM model to include intensity and gradient information, and used level-set to capture the shape statistical model information with a multi-feature landmark free framework.

Many approaches can be used in feature-based machine learning. One example includes a method to train multispectral MR imaging, such as T1, T2 and proton density weighted images, and uses parametric and non-parametric classifiers, Baysian-quadratic and k-nearest-neighbor (KNN), respectively, to segment the prostate. Another example uses a SVM-based algorithm that allows automated detection of the prostate on MR images. This method utilizes SVM binary classification on 3D MRI volumes. Automatically generated 3D features, such as median, gradient, anisotropy, and eigenvalues of the structure tensor, can be used to generate the classification binary masks for segmentation.

Applying the deep learning architecture to auto-segmentation from prostate MR images is an active new research field. One method includes a deep learning framework using independent subspace analysis to learn the most effective features in an unsupervised manner for automatic segmentation of the prostate from MR images. Another method includes a deformable automatic segmentation method by unifying deep feature learning with the sparse patch matching. Another method includes a 3D volumetric deep convolutional neural network (CNN) to model axial images and optimize the training with a Dice coefficient objective function. It utilizes a V-Net or U-net model, a 3D based convolutional and de-convolutional architecture to learn the 3D hierarchal features. Yet another method extends the 3D V-net or U-net model by incorporating symmetric residual-net layer blocks into the 3D convolutional and de-convolutional architecture.

Some methods and systems disclosed herein include an enhanced Holistically-Nested Networks (HNN) model, which can be a fully automatic prostate segmentation algorithm that can cope with the significant variability of prostate T2 MR images. Among the features of this technology is a simple and effective automatic prostate segmentation algorithm that holistically learns the rich hierarchical features of prostate MR images utilizing saliency edge maps. The enhanced HNN model can be trained with mixed Coherence Enhanced Diffusion (CED) images and T2 MR images, and can fuse the predicted probability maps from CED and T2 MR images during testing. The enhanced model is robust to prostate MR image segmentation and provides useful and promising segmentation results.

We have investigated the Alex-net Deep CNN (DCNN) model to refine the prostate boundary. The atlas-based Active Appearance Model (AAM) can serve as the first-tier of the segmentation pipeline, initializing the deep learning model by providing a rough boundary estimate for the prostate. The refinement process can then be applied to the rough boundary generated from the atlas-based AAM model in the second-tier. This is a 2D patch based pixel classification approach, which predicts the center pixel from local patches.

Figure 11C:
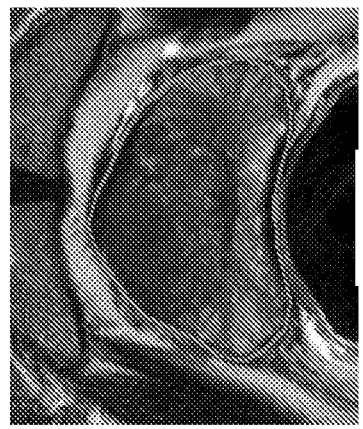
FIG. 11 illustrates Alex-net patches generation and VOIs contours prediction. Alex-net patches generation and VOIs contours prediction. (a) patches along normal line. (b) probability map. (c) final contour from probability map.
Figure 11B:
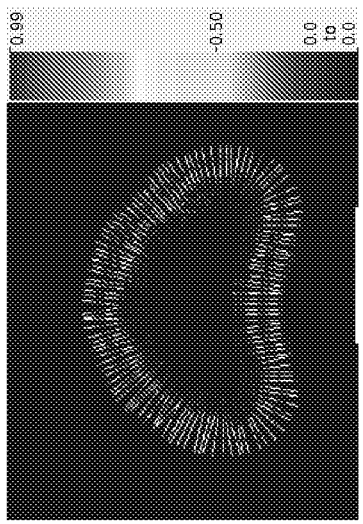
Figure 11A:
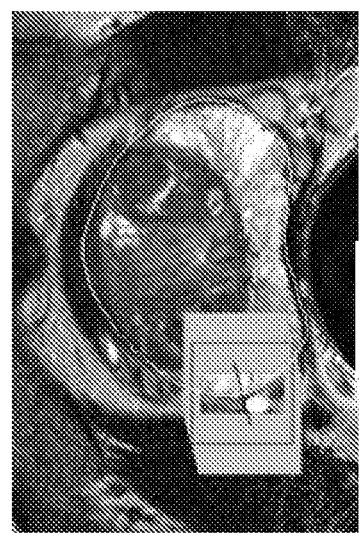

The DCNN refinement model generates the 64×64 patches along the normal line of prostate boundary. We generate a normal line (blue line) from each boundary point as shown in FIG. 11a. Each square patch is centered on the tracing point with square sides parallel to the X and Y axes. The red square patch centered on the boundary point represents positive (red box) class. The normal line of each boundary point is used as the tracing path for negative and undefined patches. We walk along the normal line 20 pixels in both inward and outward directions, collecting patches within the specified distance constraint. The green square patches on the two end points of the normal line are classified as negative patches. The pink color square patches in between are classified as undefined patches. FIG. 11a shows the 64×64 patches generated from a single normal line.

After the first-tier AAM segmentation model initializes the rough prostate boundary, the deep CNN classifier is applied to classify the unlabeled 64×64 patches around the boundary in testing. Test image patches are generated from the normal lines of the contour (FIG. 11a). Each image patch is centered on a point along a normal line with the patch square oriented parallel to the X and Y axes. During testing, all the patches are classified by the trained deep CNN model to generate energy probability maps. FIG. 11b shows the pixel based probability map along the normal line. The red color band shows the high probability candidate points of the prostate boundary. The blue and yellow bands represent the low energy candidate points. The final contour (FIG. 11c) is extracted from the probability map with the highest likelihood. A simple tracing algorithm searches for the highest likelihood point from the probability map on each normal line and fits a B-spline to these points to produce the final boundary.

Figure 12:
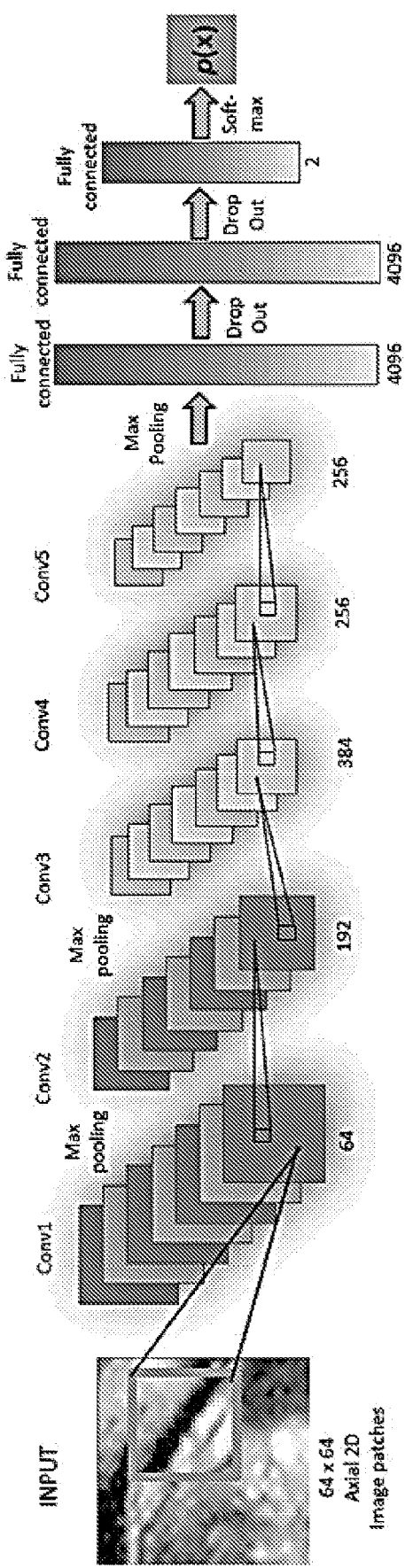
FIG. 12 illustrates Alex-net DCNN architecture.

The overall architecture of the DCNN is depicted in FIG. 12. Several layers of convolutional filters can be cascaded to compute image features in a patch-to-patch fashion from the imaging data. The whole network is executed as one primary network stream. The architecture contains convolutional layers with interleaved max-pooling layers, drop-out layers, fully connected layers, and softmax layers. This last fully-connected layer is fed to a 2-way softmax which produces a distribution over 2 class labels corresponding to probabilities for 'boundary' or 'non-boundary' image patches. The Alex-net is a first generation Deep Learning model with the training and testing constrained to fixed size patches, such as 64×64 patches. The whole architecture can be considered as a single path of multiple forward and backward propagations. To roughly estimate the number of patches being used in the training phase, with the given 250 images: 1) Each training fold (5-fold cross validation) contains 200 images. 2) Each image has around 15 VOI contours to present the prostate. 3) Each contour has 128 points. 4) Patches are traced with 40 pixels along each normal line. This simple patches collection mechanism readily creates over 15 million patches (positive, negative and non-label) to train one Alex-net deep learning model. With those 15 million patches, the last three fully connected layers in Alex-net (FIG. 12) generate a huge amount of parameter space during training. Overfitting can also easily occur. To train the model with a feasible parameters space, we discard the patches in-between the center and ending points (FIG. 11a, pink boxes, non-label) of the normal line to combat overfitting and to reduce the training patches size to around 1 million. We trained the 1 million patches directly with Alex-net architecture. No any data augmentation (i.e. rotation, flip) is conducted in the training process. GPU acceleration can help with efficient training and fast execution of the CNN in testing.

In some methods, we use the HNN architecture to learn the prostate interior image-labeling map for segmentation. The HNN model represents the second generation of the deep learning model. This type of Convolutional Neural Networks (CNNs) architecture is related to Holistically-nested Edge Detection (HED), which combines deep supervision with fully convolutional networks to effectively learn edges and object boundaries, and to resolve the challenging ambiguity problem in object detection. This can be used to detect edge and object boundaries in natural images. The HNN architecture can learn the deep hierarchical representation from general raw pixel-in and label-out mapping functions to tackle semantic image segmentation in the medical imaging domain. HNN can address at least two issues: (1) training and prediction on the whole image end-to-end, e.g., holistically, using a per-pixel labeling cost: and (2) incorporating multi-scale and multi-level learning of deep image features via auxiliary cost function at each convolution layer. HNN computes the image-to-image or pixel-to-pixel prediction maps from any input raw image to its annotated labeling map, building a fully convolutional neural networks and deeply-supervised nets. The per-pixel labeling cost function allows that HNN can be effectively trained using only several thousand annotated image pairs. This enables the automatic learning of rich hierarchical feature representations and contexts that are critical to resolve spatial ambiguity in the segmentation of organs.

Figure 13:
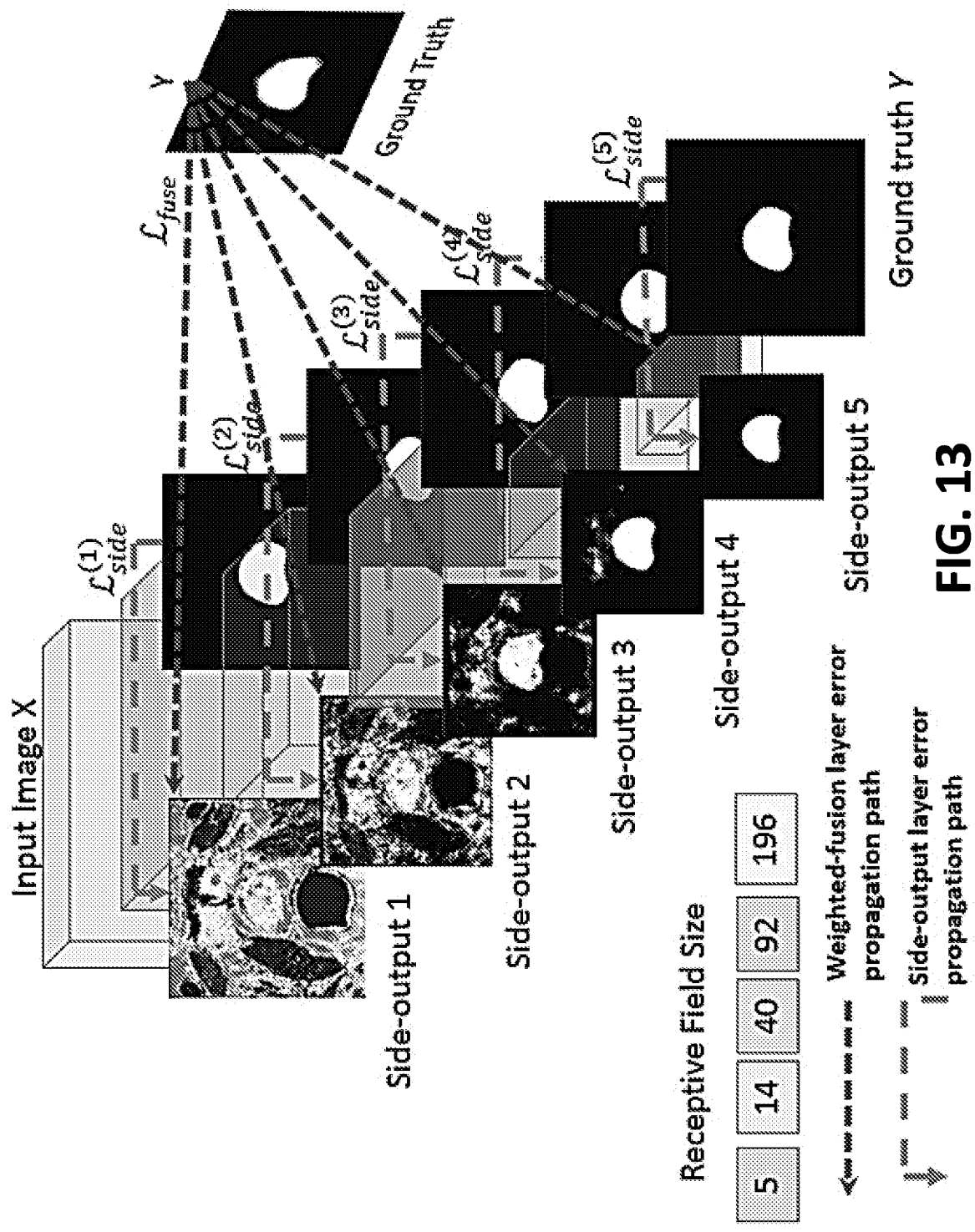
FIG. 13 is a schematic view of HNN architecture.

In contrast to the Alex-net DCNN model, Holistically-Nested Net (HNN) emphasizes an end-to-end edge detection system, and can include fully convolutional neural networks with additional deep supervision. We utilized an HNN architecture and hyper-parameter settings that were used for the Berkeley Segmentation Dataset and Benchmark (BSDS 500). Our network structures for training can be the same as for BSDS. The prostate HNN segmentation model was fine-tuned from BSDS 500 using the prostate training images. We used the VGG weights (ImageNet VGG model) for fine-tuning the prostate masks as was done when the HNN is trained on BSDS 500 parameters. The HNN networks comprise a single stream deep network with multiple side-outputs (FIG. 13), and the side-outputs are inserted after each convolutional layer. The architecture consists of 5 stages with strides of 1, 2, 4, 8, and 16. The side-output layer is a 1×1 convolutional layer of one-channel output with sigmoid activation. The outputs of HNN are multi-scale and multi-level with the side-outputs plane size becoming smaller and receptive field size becoming larger. Each side-output produces a corresponding edge map at a different scale level, and one weighted-fusion layer is added to automatically learn how to combine outputs from multi-scale, as shown in FIG. 13. The added fusion layer computes the weighted average of side-outputs to generate the final output probability map. Due to the different scale levels of side-output, all the side-outputs probability maps are up-sampled to the size of the original input image size by bilinear interpolation before fusion. The entire network is trained with multiple error propagation paths (dashed lines). With cross multiple scales, especially at the top level of the network, the trained network is heavily biased towards learning very large structure edges and missing low signal edges. Ground truth are used with each of the side-output layers to compensate the weak edge lost and play a role as deep supervision. We highlight the error back-propagation paths (red dashed lines in FIG. 13) to illustrate the deep supervision performed at each side-output layer after the corresponding convolutional layer. The fused layer also back-propagates the fused errors (blue dashed lines in FIG. 13) to each convolutional layer.

To formulate the HNN networks for prostate segmentation in training phase, we denote our training dataset as $S=\{(X_i, Y_i), i=1, \ldots, n\}$, where $X_i$ refers to the $i_{th}$ input raw image, $Y_i$ indicates the corresponding ground truth label for the $i_{th}$ input image, $Y_i \in \{0,1\}$ denotes the binary ground truth mask of prostate interior map for corresponding $X_i$.

The network is able to learn features from those image pairs along from which interior prediction maps can be produced. In addition to standard CNN layers, a HNN network has M side-output layers as shown in FIG. 13, where each side-output layer functions as a classifier with corresponding weights $w=(w^{(1)}, \ldots w^{(M)})$. All standard network layers parameters are denoted as W. The object function of the M side-output layers is, $$\mathcal{L}_{side}(W, w) = \sum_{m=1}^{M} \alpha_m l_{side}^{(m)}(W, w^{(M)})$$

where, $L_{side}$ denotes an image-level loss function for side-outputs, computed over all pixels in a training image pair X and Y. Due to the heavy bias towards non-labeled pixels in the ground truth data, a per-pixel class-balancing weight β is introduced to automatically balance the loss between positive and negative classes. A class-balanced cross-entropy loss function can be used in the equation above with j iterating over the spatial dimensions of the image:

$$\mathcal{L}_{side}^{(m)}(W, w^{(m)}) = -\beta \sum_{j \in Y_+} \log Pr(y_i = 1 | X; W, w^{(m)}) -$$

$$(1-\beta) \sum_{j \in Y_-} \log Pr(y_i = 0 | X; W, w^{(m)})$$

Where, β is simply $|Y_-|/|Y|$ and $1-\beta=|Y_+|/|Y|$, and $|Y_+|$ denote the ground truth set of negatives and positives, respectively. In contrast methods where β is computed for each training image independently, we use a constant balancing weight computed on the entire training set. This is because some training slices might not have positive classes at all, i.e. slices at the prostate at the apex and base, and otherwise would be ignored in the loss function. The class probability $Pr(y_i=1|X; W, w^{(m)})=\sigma(a_j^{(m)}) \in [0, 1]$ is computed on the activation value at each pixel j using the sigmoid function σ(•). The prostate interior map prediction $\hat{Y}(m)_{side}=\sigma(\hat{A}(m)_{side})$ can be obtained at each side-output layer, where $\hat{A}(m)_{side} \equiv \{a_j^{(m)}, j=1, \ldots, |Y|\}$ are activations of the side-output layer m. Finally, a weighted-fusion layer is added to the network that can be simultaneously learning during training. The loss function at the fusion layer is, $$\mathcal{L}_{fuse}(W, w, h) = Dist(Y, \hat{Y}_{fuse})$$

where $\hat{Y}(m)_{side}=\sigma(\Sigma_{m-1}^M h_m \hat{A}_{side})$ with $h=(h_1, \ldots, h_m)$ being the fusion weight. Dist(•) is the distance measure between the fused predictions and the ground truth label map. The cross entropy loss is used as the overall HNN loss function, which is minimized via standard stochastic gradient descent and back propagation, $$\mathcal{L}_{HNN}(W, w, h) = \operatorname{argmin}(\mathcal{L}_{side}(W, w) + \mathcal{L}_{fuse}(W, W, h))$$

During testing phase, with new image X, the prostate binary mask prediction maps $\hat{Y}_{fuse}$ and $\hat{Y}_{side}$ are generated from both side-output layers and the weighted fusion layer. HNN denotes the edge maps produced by the networks.

$$(\hat{Y}_{fuse}, \hat{Y}_{side}^{(1)} \ldots \hat{Y}_{side}^{(5)}) = HNN(X, (W, w, h))$$

Figure 14:
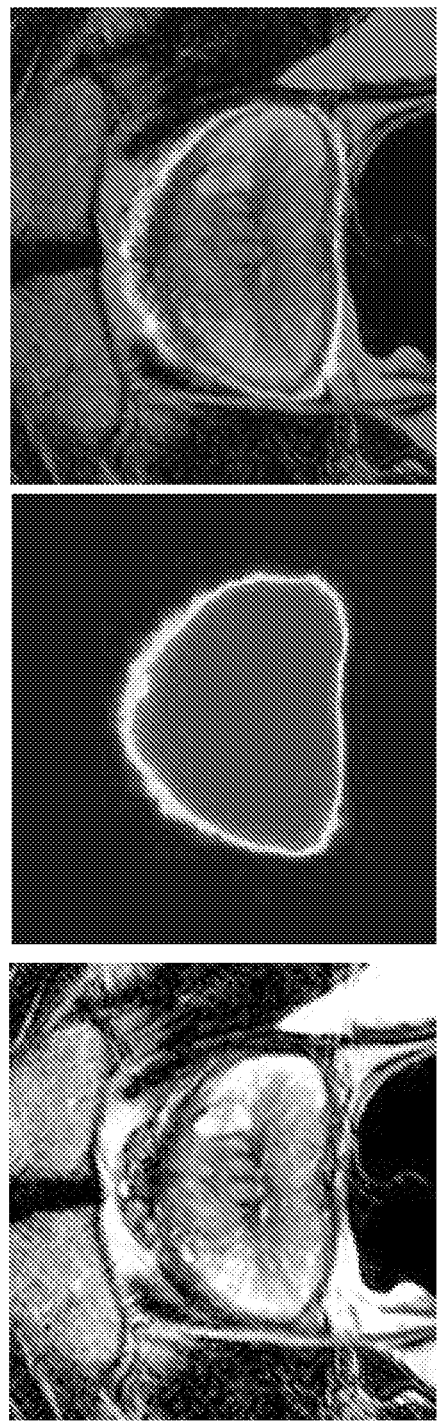
FIG. 14 illustrates a fused image with prediction probability map.

After HED prediction, the $\hat{Y}_{fuse}$ layer generated probability map is used to search the final contour. One straightforward approach is to apply the HNN model to prostate segmentation directly as shown in FIG. 13. Basically, we extract 2D slices from 3D MR images. Corresponding 2D image slice and binary mask (generated from ground truth) pairs compose the training set. During testing phase, 2D slices are extracted from 3D MR images, and run against the trained HNN model to generate the prediction probability map. A morphology operation of identifying object runs against the probability map to remove small noise regions and searches for the largest region to represent the prostate. The morphology filter generates the prostate shape binary mask from the probability map and converts the mask to the final VOI contour. The tested image fused with the probability map is shown in FIG. 14.

Applying the HNN model directly to the 2D 512×512 prostate image is a simple and effective approach. It can holistically learn the image feature for prostate interior and exterior anatomical structure. However, a few issues impose new concerns with the simple approach: 1) A 512×512 2D image contains rich anatomy information, especially, the structure outside the prostate region. Semantic learning of the large prostate exterior region may be needed. 2) The heterogeneous intensity distribution of the prostate MR image may affect the HNN model segmentation performance. The prostate boundary may need to be enhanced in case of the intensity variation. 3) Training the 2D MR images alone with one single HNN model may or may not be sufficient.

Figure 15:
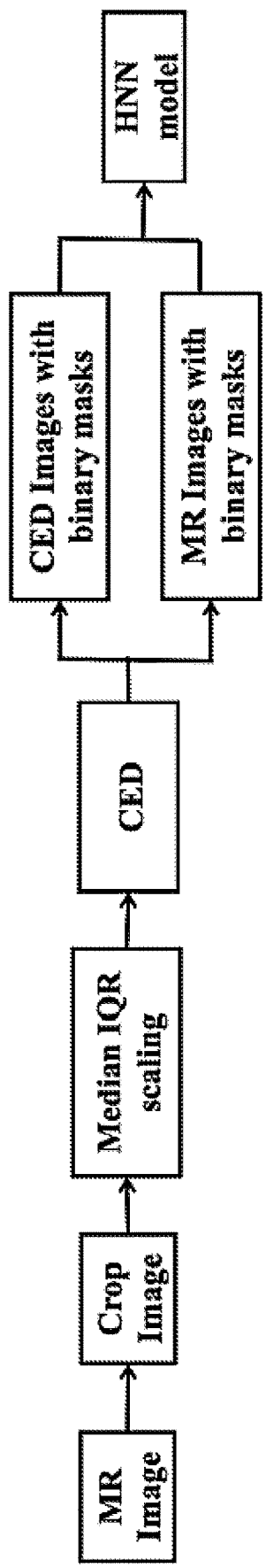
FIG. 15 illustrates an enhanced HNN model training process.
Figures 16A, 16B, 16C, 16D:
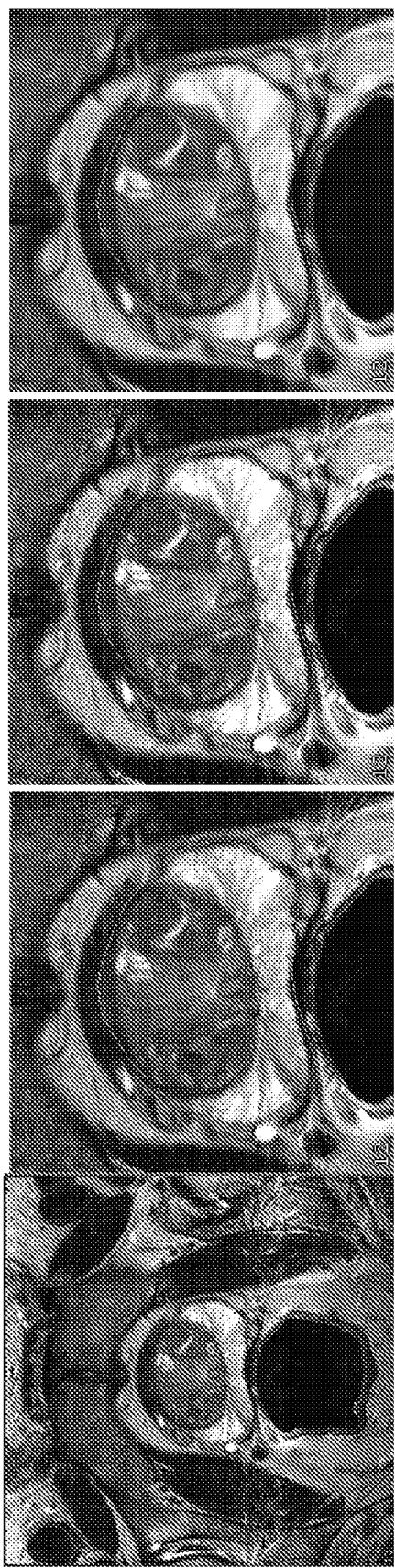
FIG. 16 illustrates an example of MR prostate image preprocessing steps: (a) The original 3D MR image slice, dimension 512×512. (b) The cropped image after 25% region reduction from top, bottom, left and right. (c) Applying median+IQR scaling to generate the MR image slices before HNN training. (d) CED applies to image after median+IQR scaling. (e) Corresponding prostate binary masks for both MR and CED images. (f) The histogram of the original MR image after cropping. (g) The histogram after applying Median+IQR with intensity scaling range from 0 to 1000, lastly rescaled to [0, 255] to fit to the PNG image format for training. After the preprocessing steps, the Median+IQR scaling generated MR image slice and the CED image slice with binary mask pairs are mixed together to train one single HNN model.
Figure 16G:
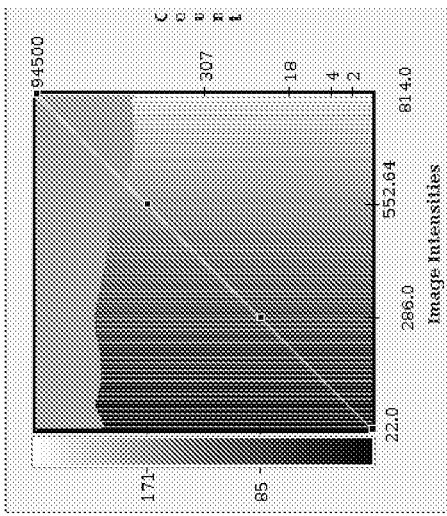
Figure 16F:
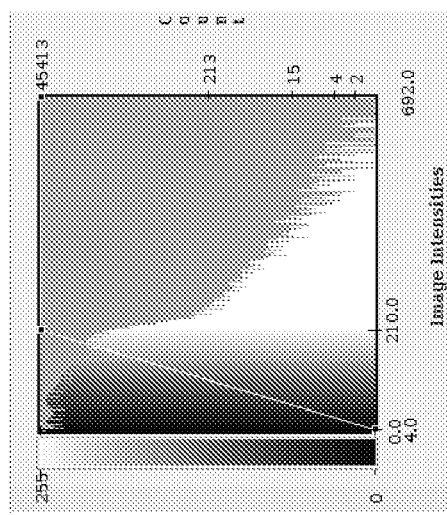
Figure 16E:
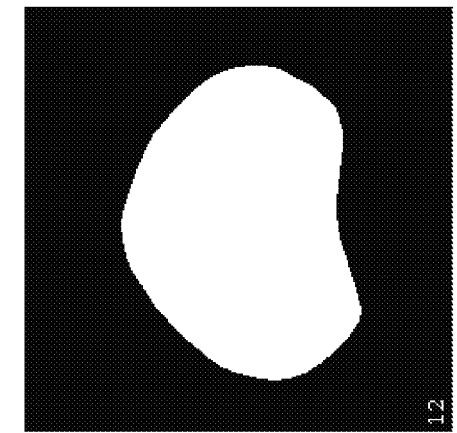

In some embodiments, an enhanced HNN model is comprised of a few major building blocks to address the above issues. FIG. 15 demonstrates the schematic pipeline diagram of the enhanced HNN model in training phase: 1) Crop the MR images from an original size of 512×512 pixels to a smaller region with focus on the prostate whole gland, 25% of pixels removed from the top, bottom, left, and right of the original image. 2) Apply the Median and Interquartile Range (IQR) to scale the cropped image intensity range between 0 and 1000, then rescale between [0, 255]. IQR is the difference between the upper and lower quantiles. The IQR can be considered a more robust measure of spread, and the median can likewise be considered a more robust measure of center tendency. In this pre-processing step, the Median and IQR scaling is calculated as, $$\hat{I}_{xyz} = 1000 * \frac{I_{xyz}}{\operatorname{median}(I) + 2*(75\%(I) - 25\%(I))}$$

where I is the intensity set of the whole cropped 3D image after sorting, and $I_{xyz}$ is the voxel intensity. Median and IQR scaling plays an alternative role to histogram equalization to work around the prostate intensity variation issue. 3) For the MR image alone, the noise and low contrast regions contribute to the major artifacts. As a consequence, some edge boundaries might be missing or blended with the surrounding tissues. We apply a Coherence Enhancing Diffusion (CED) filter to obtain the boundary enhanced feature image. CED filters relatively thin linear structures to enhance the grey level edge boundaries, which can help the HNN model efficiently learn the semantic features. 4) The cropped CED and MR images were mixed with corresponding binary masks to train one single HNN model, which enables the DCNN architecture to build up the internal correlation between CED and MR images in the neural networks. The overall image preprocessing steps are demonstrated in FIGS. 16a-16g.

Figure 17:
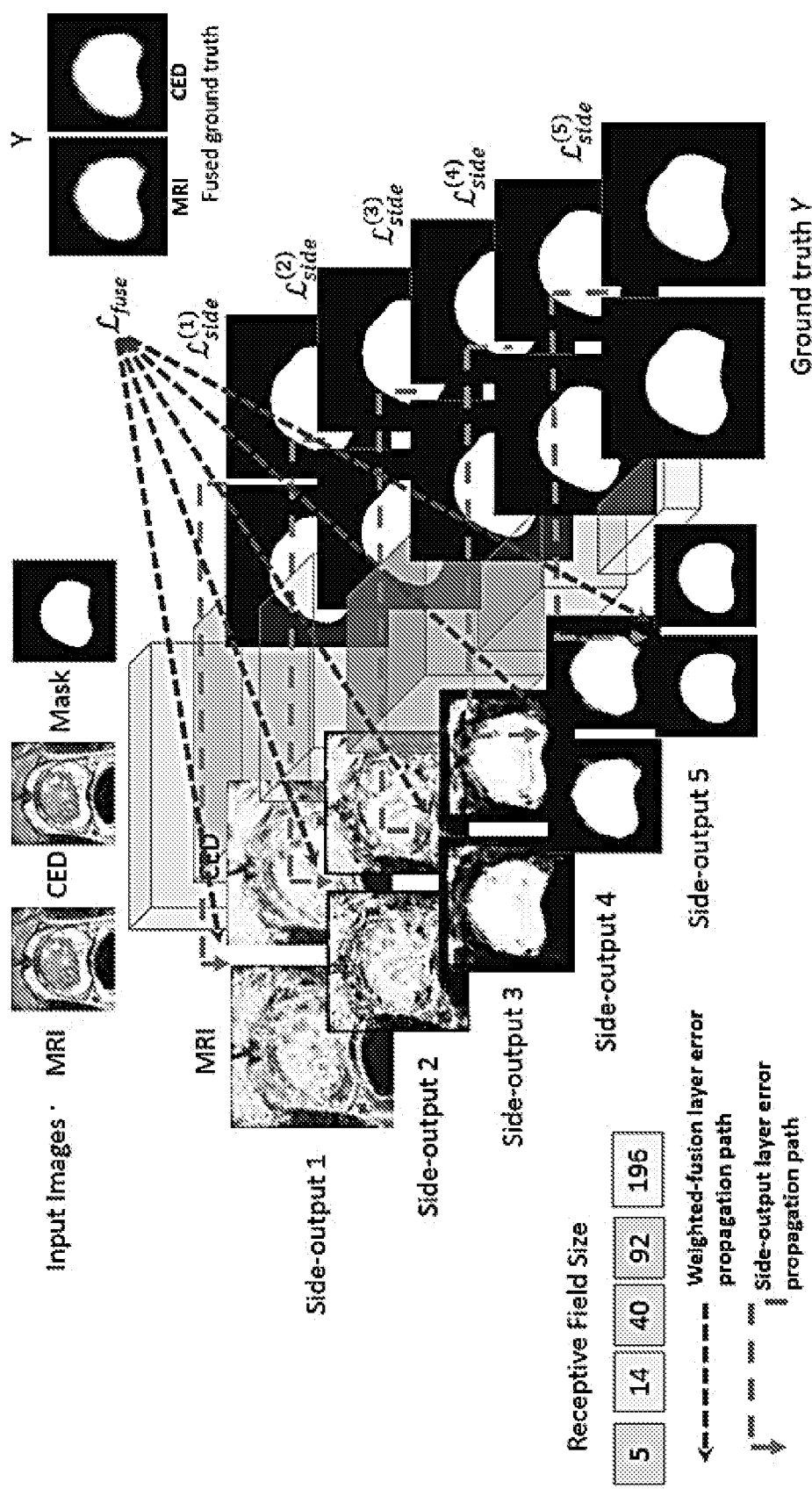
FIG. 17 is a schematic view of an enhanced HNN model.

The disclosed enhanced HNN architecture is illustrated in FIG. 17. The input of the HNN model is the mixed MRI and CED image slices with corresponding binary masks after pre-processing. Each MRI and CED slice shares with one corresponding binary mask and formulate two image slice and binary mask pairs. Each pair is standalone. At each training fold (5-fold cross validation, 200 images), several thousand independent MRI and CED pairs mix together (pair-wise) to constitute the training set. The HNN architecture still functions as a standalone model with the extended capability to handle multi-feature (multi-modality) image pairs. The HNN architecture can semantically learn the deep representation from both MRI and CED images, and build the internal CNN networks between the two image features and corresponding ground truth maps. The HNN produces per-pixel prostate probability map pairs (MRI and CED) from each side-output layer simultaneously with ground truth binary mask pairs acting as the deep supervision. This is the first time we attempt to train the different image features with a single standalone HNN model. In previous works, we already applied the HNN model to pancreas segmentation and lymph node detection in CT images. Both methods trained interior binary masks and edge boundary binary masks independently with the HNN model. During testing phase, the two HNN models generated interior probability map and edge boundary probability map are aggregated with Random Forest model to refine the final segmentation. As compared to our previous works, the disclosed enhanced HNN model takes advantage of different image features (or modalities) to train one single HNN model, which can potentially improve the reliability of the semantic image segmentation task, i.e. MRI prostate segmentation. The disclosed model lets the HNN architecture naturally learn appropriate weights and bias across different features in the training phase. When the trained network converges, we find experimentally that the $5^{th}$ layer side-out is very close to the prostate shape, which makes the fusion layer output trivial. However, the fusion layer outputs can still be used to generate the probability map. During testing phase, we can simply merge the probability maps produced from the $5^{th}$ layer MRI and CED side-outputs, and generate the final prostate boundary directly. Thus, the morphology post-processing step of training the 2D MR images alone with one single HNN model can eventually be eliminated.

Figure 18:
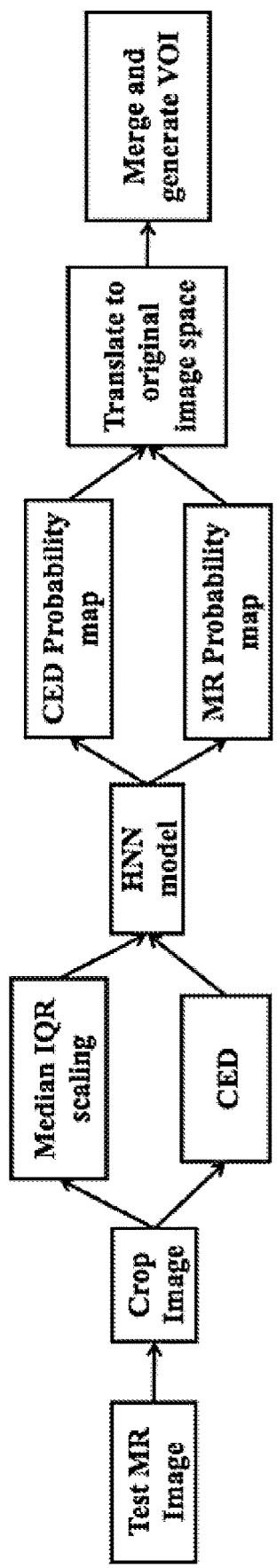
FIG. 18 illustrates an enhanced HNN model testing process.

FIG. 18 demonstrates a fully automated prostate segmentation pipeline in testing phase. First, the test image is cropped to a smaller image with 25% pixel reduction from the image boundaries. Second, the Median+IQR scaling and CED enhanced filter generate the corresponding MRI and CED 2D image slices. Third, the MRI and CED slices run against the trained HNN model to produce the probability maps simultaneously from the HNN's $5^{th}$ layer side-outputs. Fourth, the generated maps are translated into the original image space. Lastly, merge and threshold the two probability maps into a binary mask, and create the final VOI contours from the binary mask.

Figures 19A, 19B, 19C, 19D, 19E:
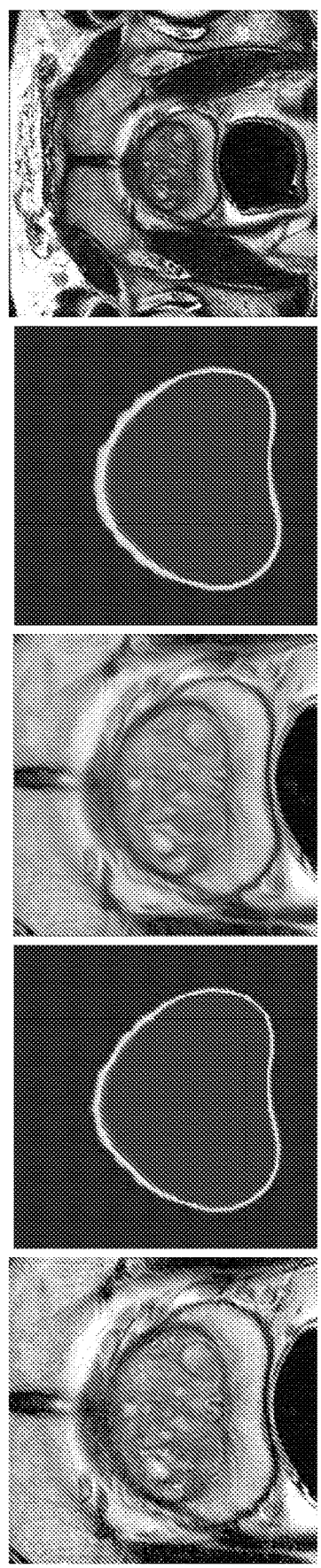
FIG. 19 shows probability maps predicted from the enhanced HNN model: (a) MRI slice. (b) MRI probability map. (c) CED slice. (d) CED probability map. (e) Final VOI contour.
Figure 20A:
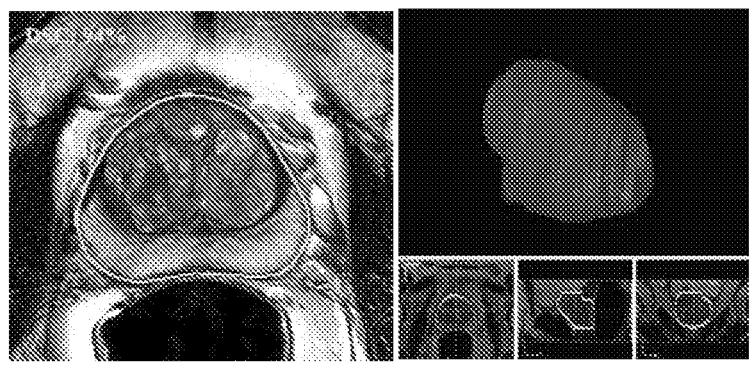
FIG. 20 shows examples of enhanced HNN model segmentation results: Ground truth (green), segmentation (red). With best performance case (a), two cases with DSC score close to mean (b, c), and the worst case (d).
Figure 20B:
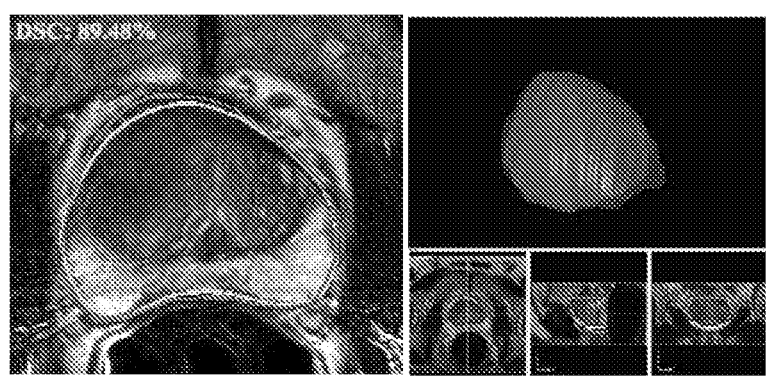
Figure 20C:
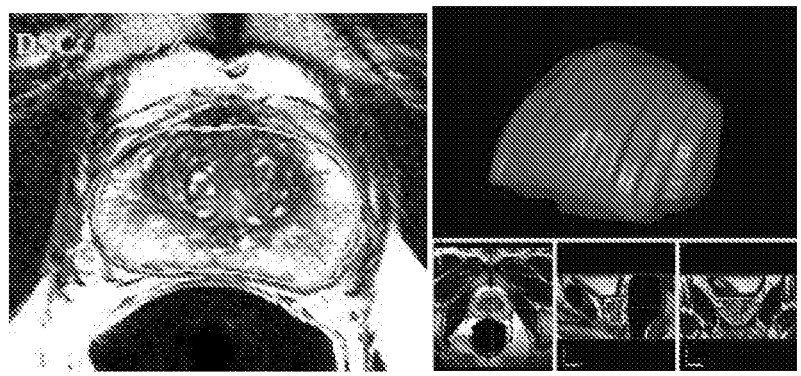
Figure 20D:
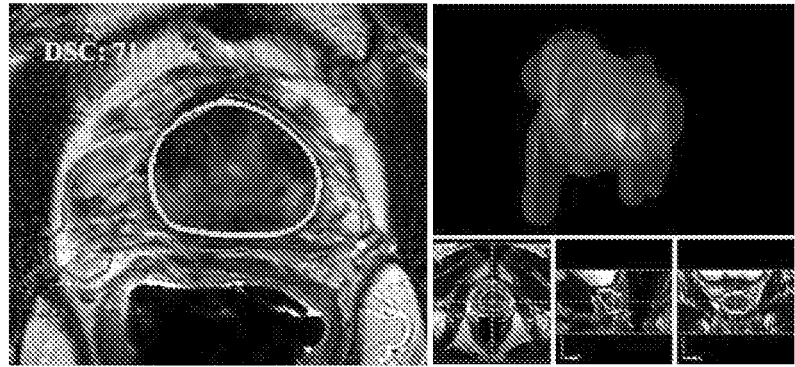

FIGS. 19(a) and (c) show the cropped MRI slice and CED slice after median+IQR scaling and rescaled in range between [0, 255]. FIGS. 19(b) and (d) are the probability maps predicted from the trained HNN model $5^{th}$ layer. FIG. 19(e) is the final prostate VOI contour generated by combining the two probability maps, then simply thresholding the largest component into a binary mask and converting it into the final boundary.

The disclosed enhanced HNN model can effectively capture the complex MRI prostate shape variation in the testing phase. The cropping image step discards non-prostate regions and allows the HNN architecture to learn finer details from the ground truth map. The prostate interior binary masks are the major mid-level cue for delineating the prostate boundary. Combining CED and MRI slice with the interior ground truth map and training with one single HNN model could be beneficial for semantic image segmentation task. During training phase, the HNN model can naturally build up the internal correlation CNNs networks across different image features (or modalities). The enhanced HNN model can elevate the overall performance of MRI prostate segmentation.

The disclosed enhanced HNN model is evaluated with 250 MR image datasets, which are provided by National Cancer Institute, Molecular Imaging Branch. The MR images are obtained from a 3.0 T whole-body MRI system. T2-weighted MR images of the entire prostate were obtained in axial plane at the scan resolution of 0.2734×0.2734×3.0 $mm^3$; field of view 140 mm; image slice dimension 512× 512. The center of the prostate is the focal point for the MRI scan. All the images are acquired using an endorectal coil, which is used routinely for imaging the prostate. The prostate shapes and appearance impose large variation across different patients. There is a wide variation in prostate shape in patients with and without cancer that incorporates variability relating to prostate hypertrophy and ECE (capsular penetration). However, in our cases, there were a few examples of ECE that caused marked prostatic boundary distortion. The impact of capsular involvement is a minor factor to affect our segmentation algorithm accuracy. Among all the 250 cases, almost all prostates have abnormal findings, mainly due to BPH (Benign Prostatic Hyperplasia), which causes all prostates look different. Although most cases include cancer in our population it is uncommon for the capsule of the prostate to be affected by cancer and thus the segmentation. Each image is related to one patient with corresponding prostate VOIs contours. The gold standard contour VOIs are obtained from the expert manual segmentation, which is made and verified by a radiologist. These VOIs are considered as the ground truth of the evaluation. The axial T2W MR image were manually segmented in a planimetric approach (slice-wise contouring of the prostate in axial view) by an experienced genitourinary radiologist using a research-based segmentation software. Those segmentations are all done when the patients are being read clinically.

With the given 250 images, our experiments are conducted on splits of 200 images for training and the other 50 images for testing in 5-fold cross-validation. Each fold is trained with one deep learning model independently of each other. Three experiments are conducted for each fold to evaluate the final segmented VOI contours with the ground truth VOI contours in binary mask based comparison.

We briefly describe the training process of each experiment. 1) Alex-net model: 2D 64×64 patches (Positive and Negative) are collected along the normal line as described in Section 2.1 from the 200 images. The generated 1 million patches oriented parallel to X and Y axes are used to train one Alex-net deep learning model. 2) HNN_mri model: Around 5 thousand 2D MR image slices and corresponding VOI binary mask pairs are used to train one HNN model. Those image pairs are fine-tuned with the BSDS 500 architecture and hyper-parameter setting to generate the prostate specific HNN model. 3) HNN_mri ced model: After the preprocessing step, around 10 thousands 2D MR image slices and binary mask pairs and 2D CED and binary mask pairs are mixed (pair-wise) together to train one standalone HNN model. During testing phase, the rest 50 images (in each fold) run against each trained model to generate the probability maps. For each method, we use a different strategy to extract the VOI contours from the probability map. 1) Alex-net approach: We identify the highest probability point along the normal line and use B-Spline to smooth the final VOI contours. 2) HNN-mri standalone model: We utilize the morphology with identity object operation to filter out the largest region from the probability map, and convert it to the final VOIs. 3) HNN mri ced multi-feature standalone model: We directly threshold the probability map from the fifth side-output layer to generate the final VOI contours. The performance evaluation is binary mask based comparison by converting the final VOI contours to binary masks.

The segmentation performance (Table 3) was evaluated with (1) Dice similarity coefficient (DSC), (2) Jaccard (IoU), (3) Hausdorff distance (HDRFDST mm), and (4) Average minimum Surface-to-Surface Distance (AVGDIST, mm). All the metrics are calculated without trimming any ending contours or cropping data to the [5%, 95%] probability interval to avoid outliers for distance based measure. The mask based performance measure uses the Evaluate Segmentation tool to compare the ground truth and segmented masks. Statistical significance of differences in performance between the disclosed deep learning models is determined using the Wilcoxon Signed Rank Test to compute the p value, for DSC, IoU and HDRFDST. The HNN model with MRI alone elevates the mean DSC from 81.03% to 86.86% ($p<0.001$) and the mean IoU from 68.57% to 77.48% ($p<0.001$), which is a significant improvement over the Alex-net deep learning model used for contour refinement. The enhanced HNN model (MRI+CED) further boosts the segmentation performance by 3% ($p<0.001$) from HNN MRI standalone model in both DSC and IoU. Those results demonstrate that to train one single HNN model across different image features (or modalities) can essentially improve the reliability of semantic image segmentation. In case of MRI prostate segmentation, the enhanced HNN model can capture the complex prostate shape variation in the testing phase. The enhanced model also achieves Hausdorff distance of 13.52±7.87 mm ($p<0.001$), which indicates that HNN MRI+CED is more robust than HNN MRI alone and AAM Alex-net models in the worst case scenario.

Hausdorff distance are primarily contributed from the erroneous contours at apex and base. Overall, the disclsoed enhanced HNN model could be highly generalizable to other medical imaging segmentation tasks.

The first AAM+Alex-net method was composited from two major building blocks. The first building block implemented the Stegmann et al. AAM model in MIPAV with Java. The traditional AAM standalone model required many images and VOIs to capture shape variations. Training a single AAM model with large numbers of image textures and VOIs always generates an irregular shape and unstable segmentation in practice. We implemented the atlas based AAM training with subgroups to ensure that relatively similar image and VOIs shapes can be trained with a higher number of eigenvalues in the PCA model. An exhaustive searching algorithm with the atlas generates many groups to capture the shape and texture variations. This atlas based AAM strategy can reduce the segmentation errors. After the AAM model generates the initial VOI contours, we apply the patches based Alex-net deep learning model to refine the boundary. Rectified linear units are used as the neuron model instead of the standard neuron model $f(x)=\tan h(x)$ and $f(x)=(1-e^{-x})^{-1}$. For each training fold, we applied the random sampling to the training set, which divides the training set into a random training subset and a testing subset. However, we did not apply random initialization to the 1M patches before training.

Figure 21:
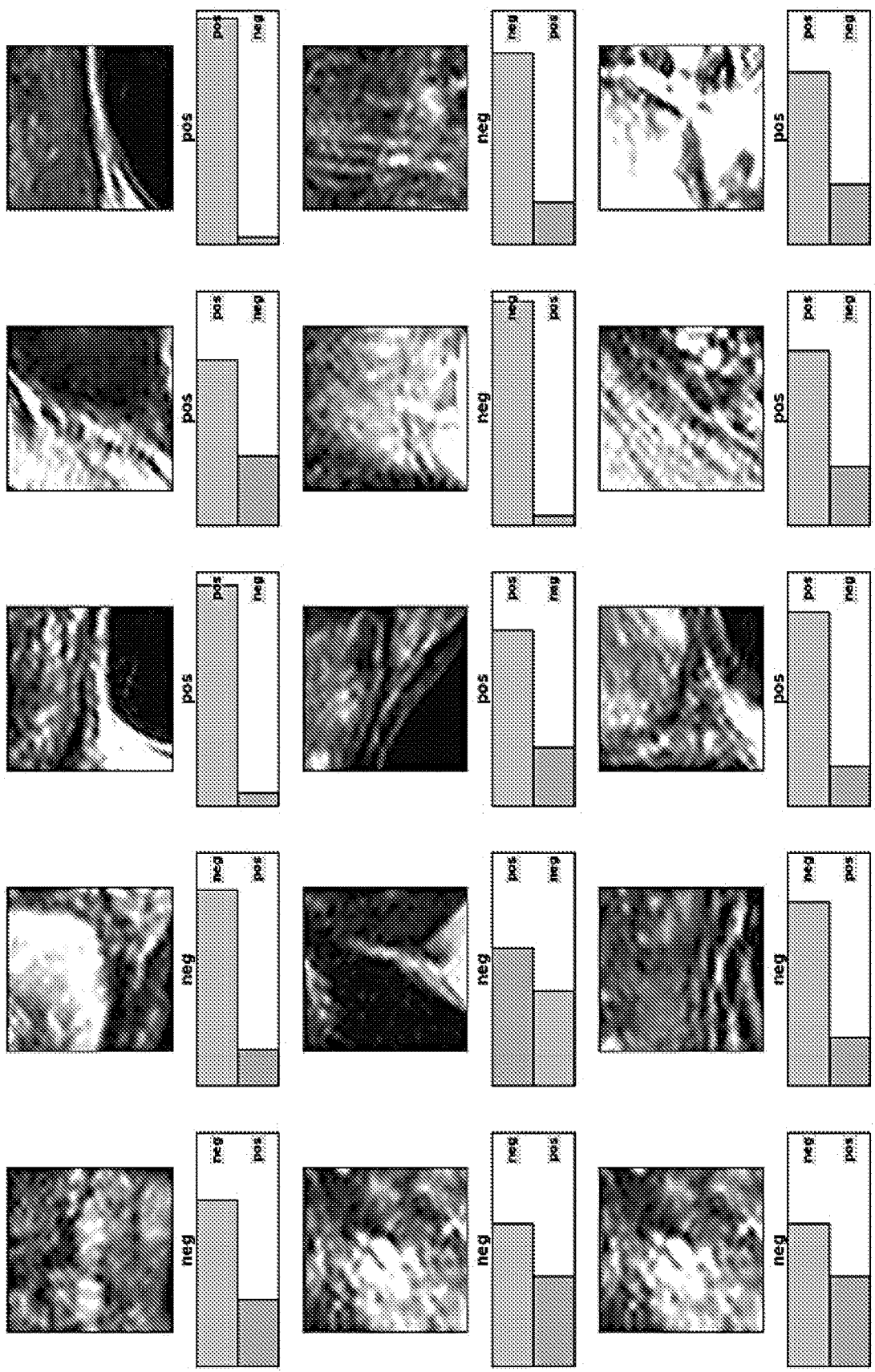
FIG. 21 illustrates test case prediction with Alex-net CNN.

To qualitatively access how well the CNN network had learned the prostate boundary, FIG. 21 demonstrates typical classification probabilities on a random subset of 'positive' and 'negative' image patches for one test case. The probability for each patch of being centered on the prostate boundary ('positive'), and for being off the boundary ('negative') are shown. The correct ground truth label is written under each image patch. The category with the highest CNN probability is shown as the top bar and is displayed in pink if correctly classified—violet if incorrectly classified. With data augmentation, we rotate each patch 90, 180, and 270 degrees, and flip each patch in X and Y axes. This approach downgrades the training and testing time, and yields no improvements in both Dice score and Hausdorff distance.

TABLE 3

Testing phase 5-fold cross validation: The quantitative MRI prostate segmentation performance results of comparing AAM + Alex_net (Alex), HNN MRI alone (HNNmri), HNN MRI + CED (HNNced) methods in four metrics of DSC (%), Jaccard Index (IoU) (%), Hausdorff distance (HDRFDST [mm]), and Average minimum surface-to-surface distance (AVGDIST [mm]).

| | DSC | | | Jaccard (IoU) | | | HDRFDIST | | | AVGDIST | | |
|---|---|---|---|---|---|---|---|---|---|---|---|---|
| | Alex | HNNmri | HNNced | Alex | HNNmri | HNNced | Alex | HNNmri | HNNced | Alex | HNNmri | HNNced |
| Mean | 81.03 | 86.86 | 89.77 | 68.58 | 77.48 | 81.59 | 15.25 | 17.41 | 13.52 | 0.37 | 0.34 | 0.16 |
| Std | 6.34 | 7.60 | 3.29 | 8.72 | 10.50 | 5.18 | 9.27 | 11.72 | 7.87 | 0.22 | 0.54 | 0.08 |
| Median | 82.34 | 89.30 | 90.33 | 69.98 | 80.66 | 82.37 | 12.54 | 13.20 | 11.33 | 0.32 | 0.16 | 0.13 |
| Min | 56.45 | 52.07 | 71.13 | 39.32 | 35.20 | 55.20 | 4.12 | 4.24 | 4.24 | 0.08 | 0.06 | 0.06 |
| Max | 94.39 | 94.65 | 94.62 | 89.39 | 89.84 | 89.79 | 55.52 | 93.10 | 63.54 | 1.68 | 4.04 | 0.69 |

Best performance methods are shown in bold.

Few examples of patient cases are shown in FIG. 20. The green color present the ground truth, the red color present the segmentation results of the enhanced HNN model. FIG. 20 also illustrates the 3D surfaces overlapping between our model generated surface and the ground truth surface for each patient. Perceptually, the disclosed method shows promising segmentation results from the best, normal and worst cases. Noticeable volume difference and high We used the generated patches to train the Alex-net deep learning model directly without any data augmentation.

For the second HNN mri standalone method, we utilized the HED implementation (C++ and Python) as the base HNN architecture. The method was implemented using the latest Caffe library and build on top of the FCN and DSN. We utilized the same HNN architecture and hyper-parameter settings of BSDS 500. We also used the VGG weights for fine-tuning the prostate masks when the HNN is trained on BSDS 500. The hyper-parameters (choosing values) include: batch size (1), learning rate (10e-7), momentum (0.9), weight decay (0.0002), number of training iterations (30000; divide learning rate by 10 after 10000 iterations). We also implemented MIPAV Java routines to handle image processing and VOI extraction from the probability maps after HNN prediction. A threshold filter [240, 255], first applied to the probability map, which is generated from fusion layer side-output and scaled from [0, 1] to [0, 255]. Then, a morphology operation of identifying objects (MIPAV) with flood value 1 is applied to flood filling all possible regions and filtering out the largest region to represent the prostate. Finally, convert the 2D region mask to VOI contours.

For the third Alex_mri_ced single standalone HNN method, we simply used the standalone HNN model in the second method without any modification, and implemented a Java wrapper in MIPAV to handle the pre-processing step, multi-features (multi-modality) image I/O and dual probability maps interpolation after the HNN prediction. When we trained the model, multi-feature image pairs (MM and CED 2D slices with binary masks) were fed into the single standalone HNN architecture and let the networks naturally build the deep representation among multi-feature images. The Coherence Enhanced Diffusion (CED) filter was implemented in MIPAV with the follow parameters: derivative scale (0.5), Gaussian scale (2.0), number iterations (50), 25D (true). After the HNN prediction generating the MRI and CED probability maps from the fifth side-output layer, we fused the two maps into one, and simply applied the threshold filter [240, 255] to build the largest region mask and convert it to final VOI contours.

The AAM+Alex-net method, the approximate elapse time to train one AAM model is around two hours for 200 images in each fold. To train the patches based Alex-net deep learning model, it takes about 5 days to train just one model on single Titan Z GPU. Once trained, the average running time for each test image is as follows: the AAM model takes 3 minutes to generate the initial VOIs contours. Patches generation from the initial contours, predicting the probability map from Alex-net model, and converting the map to final VOIs contours combine together take around 5 minutes. Thus, the complete processing time for each test image is around 8 minutes.

Training on HNN_mri standalone model takes about 2 days on a single NVIDIA Titan Z GPU. For a typical test image (512×512×26), it takes HNN model under 2 seconds to generate the probability, and 1 second for the Java routine to convert the probability map into the final VOIs. The total segmentation time for each test image is 3 seconds, which is significantly faster than the AAM+Alex-net method.

The HNN_mri_ced method spends extra time to handle the preprocessing and post-processing steps. The CED filter is a time consuming step, which takes about 30 seconds for each image to generate the CED image. Training HNN model based on the MRI and CED pairs from each fold takes 2.5 days on a single Titan Z card. The whole processing time for each test image to generate the final VOIs contours is around 2 minutes.

The disclosed enhanced HNN model performs very well for MRI prostate segmentation with reported mean DSC (89.77%±3.29%) in the 5-fold cross validation. Table 4 shows a rough comparison of our method to selected other methods. The qualitative data shows that our method produces relatively reliable MRI prostate segmentation without trimming any erroneous contours at apex and base, i.e. trimming end contours at 5%, or $\alpha=0.95$.

TABLE 4

Quantitative comparisons between disclsoed method and other notable methods from the literature.

| Methods | DSC + Stdev(%) | HDRFDIST(mm) | AVGDIST(mm) | Images | Evaluation | Trim($\alpha$: 0.95) |
|---|---|---|---|---|---|---|
| Klein | 84.40 ± 3.10 | 10.20 ± 2.60 | 2.50 ± 1.40 | 50 | Leave-one-out | Yes |
| Toth | 87.66 ± 4.97 | | 1.51 ± 0.78 | 108 | 5-fold validation | Yes |
| Liao | 86.70 ± 2.20 | 8.20 ± 2.50 | 1.90 ± 1.60 | 30 | Leave-one-out | Yes |
| Guo | 87.10 ± 4.20 | 8.12 ± 2.89 | 1.66 ± 0.49 | 66 | 2-fold validation | Yes |
| Melletari | 86.90 ± 3.30 | 5.71 ± 1.20 | | Promise12(80) | Train: 50, test: 30 | Yes |
| Yu | 89.43 | 5.54 | 1.95 | Promise12(80) | Train: 50, test: 30 | Yes |
| Korsager | 88.00 ± 5.00 | | 1.45 ± 0.41 | 67 | Leave-one-out | Yes |
| Chilali | 81.78 ± 5.86 | | 3.00 ± 1.50 | Promise12(80) | Train: 50, test: 30 | Yes |
| HNNmri + ced | 89.77 ± 3.29 | 13.52 ± 7.87 | 0.16 ± 0.08 | 250 | 5-fold validation | No |

The measured running time revealed that two HNN based methods outperform the patch based Alex-net method in both training and testing phases. This is primarily due to the huge parameter space created during convolution by Alex-net architecture. The multi-scale and multi-level HNN architecture converges faster than the Alex-net counterpart because of the removal of the fully connected layers from VGGNet 16 and replacement with the side-output layers. Although the enhanced HNN_mri_ced model spends extra time to perform image pre and post processing steps, the multi-features training and prediction mechanism improves the segmentation performance by 3% from the HNN_mri standalone model. Thus, the disclsoed enhanced HNN model is a better choice than the Alex_net model in both processing time and segmentation performance.

The Alex-net is a first generation Deep Learning model with the training and testing constrained to fixed size patches, such as 64×64 patches. The Alex-net DCNN model focuses on automatic feature learning, multi-scale convolution, and enforcement of different levels of visual perception. However, the multi-scale responses produced at the hidden layers are less meaningful, since feedback is usually back-propagated through the intermediate layers. The patch-to-pixel and patch-to-patch strategy significantly downgrades the training and prediction efficiency. Some drawbacks of Alex-net are: 1) A huge parameter space is created from the last three fully connected layers, which downgrades the training performance and limits the number of patches being trained on a single graphics card. 2) With unbalanced patch labeling, the Alex-net model easily runs into overfitting. 3) Each patch (64×64) is convolved to maintain a hierarchical relation inside the patch itself. There is no contextual or correlation information between patches during the training phase.

The HNN_mri model represents an improvement of the deep learning model. In contrast to the Alex-net DCNN model, Holistically-Nested Net (HNN) emphasizes an end-to-end detection system, a system inspired by fully convolutional neural networks with deep supervision on top of VGGNet 16. Advantages over the first generation Alex-net model include: 1) Training and prediction on whole image end-to-end using per-pixel labeling cost. 2) Incorporating multi-scale and multi-level learning via multi-propagation loss. 3) Computing the image-to-image or pixel-to-pixel prediction maps from any input raw image to its annotated labeling map. 4) Integrated learning of hierarchical features. 5) Much faster performance than Alex-net model due to the fact that HNN produces the segmentation for each slice in one single steam line path, and speeds up the processing time without running the segmentation for each of many patches.

The enhanced HNN_mri_ced model imposes multi-features (multi-modality) into the single standalone HNN model. To address the three concerns from the single standalone HNN_mri model, the enhanced model, 1) Utilizes cropping to remove large non-prostate regions and makes the HNN training more accurate and efficient. 2) Median+IQR filter normalizes the MR images to curb the large intensity distribution variation issue. 3) CED and MR slices are fed into the single standalone HNN architecture to let the HNN model naturally learn and build the deep representation from multi-features and multi-scale, to enhance the HNN prediction reliability.

In conclusion, we present a holistic deep CNN approach for automatic Mill prostate segmentation, exploiting the multi-features (MRI+CED, or modalities) training with one single HNN model, generating robust segmentation results by fusing Mill and CED predicted probability maps. Previous Alex-net deep learning approach typically used a patch-based system, which can be inefficient in both training and testing, and has limited segmentation accuracy. The disclosed enhanced HNN model can incorporate multi-scale and multi-level feature learning across multiple image features (or modalities), and immediately produces and fuses multi-scale outputs in an image-to-image fashion. The enhanced HNN model elevates the segmentation performance from the Alex-net deep learning model by 9% in mean DSC and 13% in mean IoU, which significantly ($p<0.001$) improves the segmentation accuracy. In addition, the disclosed model achieves close to state-of-the-art performance as compared to other literature approaches. The enhanced HNN model with multi-features (or modalities) approach is generalizable to other medical imaging segmentation tasks, such as organs or tumors in related methods.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically, chemically, electrically, magnetically, or otherwise coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. A method of detecting prostate cancer from multi-parametric magnet resonance imaging (mpMRI) data for a prostate, the method comprising:
receiving mpMRI data for a prostate;
producing prostate cancer probability images from the mpMRI data using pixel-wise Random Forest machine learning applied to the mpMRI data; and
determining potential biopsy sites in the prostate based on the prostate cancer probability images;
wherein producing the prostate cancer probability images from the mpMRI data comprises using a signed Euclidean distance to a transition zone as a feature to specialize on peripheral and transition zones.

2. The method of claim 1, wherein mpMRI data includes T2W, ADC, and B2000 MRI images.

3. The method of claim 1, wherein producing the prostate cancer probability images from the mpMRI data comprises using instance-level weighting.

4. The method of claim 1, wherein the pixel-wise Random Forest is trained against plural types of annotations, including hand-drawn contours, targeted biopsies, and normal cases.

5. The method of claim 1, wherein producing prostate cancer probability images from the mpMRI data using pixel-wise Random Forest machine learning comprises using Haralick texture features.

6. The method of claim 1, wherein producing prostate cancer probability images from the mpMRI data using pixel-wise Random Forest machine learning comprises using intensity features applied to the mpMRI data.

7. The method of claim 1, further comprising using AutoContext.

8. A system configured to perform the method of claim 1.

9. A computer-readable storage device comprising computer-executable instructions, which when executed by a computing system, are capable of causing the computing system to perform the method of claim 1.

* * * * *